United States Patent
Nagashima et al.

(10) Patent No.: US 8,596,931 B2
(45) Date of Patent: Dec. 3, 2013

(54) PARTICULATE WATER ABSORBING AGENT AND METHOD FOR PRODUCING THE SAME

(75) Inventors: Teruhisa Nagashima, Himeji (JP); Masatoshi Nakamura, Himeji (JP); Yusuke Watanabe, Himeji (JP); Kozo Nogi, Kakogawa (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 530 days.

(21) Appl. No.: 12/593,443

(22) PCT Filed: Mar. 28, 2008

(86) PCT No.: PCT/JP2008/056168
§ 371 (c)(1),
(2), (4) Date: Sep. 28, 2009

(87) PCT Pub. No.: WO2008/120742
PCT Pub. Date: Oct. 9, 2008

(65) Prior Publication Data
US 2010/0119312 A1 May 13, 2010

(30) Foreign Application Priority Data
Mar. 29, 2007 (JP) .................................. 2007-089601

(51) Int. Cl.
*B65G 53/00* (2006.01)
(52) U.S. Cl.
USPC ................. 406/197; 406/46; 406/47; 406/198
(58) Field of Classification Search
USPC ....................................... 406/46, 47, 197, 198
See application file for complete search history.

(56) References Cited

U.S. PATENT DOCUMENTS

| | | | | |
|---|---|---|---|---|
| 4,342,858 A | * | 8/1982 | Herman et al. | 525/327.8 |
| 4,401,795 A | * | 8/1983 | Herman et al. | 525/327.8 |
| 4,666,983 A | * | 5/1987 | Tsubakimoto et al. | 525/119 |
| 5,085,787 A | * | 2/1992 | Pinschmidt et al. | 507/221 |
| 5,314,952 A | * | 5/1994 | Choi et al. | 525/119 |
| 5,339,769 A | * | 8/1994 | Toth et al. | 119/173 |

(Continued)

FOREIGN PATENT DOCUMENTS

| CA | 2 426 802 | 4/2003 |
|---|---|---|
| CA | 1970586 | 5/2007 |

(Continued)

OTHER PUBLICATIONS

International Search Report for PCT/JP2008/056168, mailed May 20, 2008.

(Continued)

*Primary Examiner* — Joseph Dillon, Jr.
(74) *Attorney, Agent, or Firm* — Nixon & Vanderhye, PC

(57) ABSTRACT

A method includes the steps of: adding an organic surface cross-linking agent to a water absorbent resin having a cross-linked structure; adding a liquid permeability improving agent to the water absorbent resin concurrently with or after the addition of the organic surface cross-linking agent; and then adding a lubrication improving agent to the water absorbent resin. This provides a particulate water absorbing agent and a method for producing it, the particulate water absorbing agent being suitable for pneumatic transportation, suffering no decrease in the effect of the liquid permeability improving agent, and excelling in properties such as fluidity and damage resistance after the pneumatic transportation.

16 Claims, 1 Drawing Sheet

(56) References Cited

U.S. PATENT DOCUMENTS

| | | | |
|---|---|---|---|
| 5,374,684 A * | 12/1994 | Tai | 525/254 |
| 5,397,626 A * | 3/1995 | Berg et al. | 442/393 |
| 5,492,962 A * | 2/1996 | Lahrman et al. | 524/556 |
| 5,536,264 A * | 7/1996 | Hsueh et al. | 604/368 |
| 5,684,106 A | 11/1997 | Johnson et al. | |
| 6,239,230 B1 * | 5/2001 | Eckert et al. | 525/329.9 |
| 6,376,618 B1 * | 4/2002 | Mitchell et al. | 525/329.9 |
| 6,391,451 B1 * | 5/2002 | Mitchell et al. | 428/402 |
| 6,727,345 B2 * | 4/2004 | Kajikawa et al. | 528/502 R |
| 6,803,107 B2 * | 10/2004 | Mitchell et al. | 428/403 |
| 6,911,499 B1 * | 6/2005 | Brehm et al. | 525/329.7 |
| 7,169,843 B2 | 1/2007 | Smith et al. | |
| 7,193,006 B2 * | 3/2007 | Ishizaki et al. | 524/500 |
| 7,429,632 B2 * | 9/2008 | Mitchell | 525/326.6 |
| 7,473,739 B2 | 1/2009 | Dairoku et al. | |
| 7,495,056 B2 * | 2/2009 | Torii et al. | 524/522 |
| 7,510,988 B2 * | 3/2009 | Wada et al. | 442/375 |
| 7,582,705 B2 * | 9/2009 | Dairoku et al. | 525/379 |
| 7,638,570 B2 * | 12/2009 | Torii et al. | 524/430 |
| 7,795,345 B2 * | 9/2010 | Smith et al. | 524/556 |
| 7,851,550 B2 * | 12/2010 | Kadonaga et al. | 525/53 |
| 7,919,564 B2 * | 4/2011 | Shibata et al. | 525/329.7 |
| 8,017,549 B2 * | 9/2011 | Herfert et al. | 502/402 |
| 8,148,485 B2 * | 4/2012 | Nogi et al. | 526/317.1 |
| 8,188,163 B2 * | 5/2012 | Matsumoto et al. | 523/330 |
| 8,247,640 B2 * | 8/2012 | Jonas et al. | 604/372 |
| 8,252,715 B2 * | 8/2012 | Torii et al. | 502/402 |
| 8,410,223 B2 * | 4/2013 | Matsumoto et al. | 525/330.2 |
| 8,436,090 B2 * | 5/2013 | Dairoku et al. | 524/556 |
| 2003/0020199 A1 * | 1/2003 | Kajikawa et al. | 264/140 |
| 2003/0087983 A1 * | 5/2003 | Kajikawa et al. | 522/150 |
| 2003/0219600 A1 * | 11/2003 | Mitchell et al. | 428/407 |
| 2004/0110006 A1 * | 6/2004 | Ishizaki et al. | 428/402 |
| 2004/0213892 A1 * | 10/2004 | Jonas et al. | 427/2.3 |
| 2004/0214946 A1 | 10/2004 | Smith et al. | |
| 2005/0013992 A1 * | 1/2005 | Azad et al. | 428/327 |
| 2005/0113252 A1 * | 5/2005 | Miyake et al. | 502/402 |
| 2005/0209352 A1 | 9/2005 | Dairoku et al. | |
| 2007/0149691 A1 * | 6/2007 | Ishizaki et al. | 524/500 |
| 2007/0167560 A1 | 7/2007 | Smith et al. | |
| 2007/0203304 A1 * | 8/2007 | Mitchell | 525/330.3 |
| 2008/0269372 A1 | 10/2008 | Dairoku et al. | |
| 2009/0264845 A1 * | 10/2009 | Himori et al. | 604/367 |
| 2009/0321682 A1 * | 12/2009 | Kajikawa et al. | 252/194 |
| 2010/0093949 A1 * | 4/2010 | Herfert et al. | 525/451 |
| 2010/0160883 A1 * | 6/2010 | Jonas et al. | 604/368 |
| 2011/0009590 A1 * | 1/2011 | Matsumoto et al. | 526/317.1 |
| 2011/0088806 A1 * | 4/2011 | Nogi et al. | 141/1 |
| 2011/0110730 A1 * | 5/2011 | Nogi et al. | 406/197 |
| 2012/0231162 A1 * | 9/2012 | Weismantel et al. | 427/222 |
| 2012/0289671 A1 * | 11/2012 | Takaai et al. | 526/240 |
| 2012/0298915 A1 * | 11/2012 | Okuda et al. | 252/194 |
| 2013/0005926 A1 * | 1/2013 | Kanzaki et al. | 526/317.1 |
| 2013/0066019 A1 * | 3/2013 | Okuda et al. | 525/329.7 |

FOREIGN PATENT DOCUMENTS

| | | |
|---|---|---|
| JP | A-2004-345804 | 12/2004 |
| TW | 2007-20346 | 6/2007 |
| WO | 2005/097313 | 10/2005 |

OTHER PUBLICATIONS

Japanese Office Action issued in Japanese Patent Application No. 2008-532934, mailed May 14, 2013 (with translation).

* cited by examiner

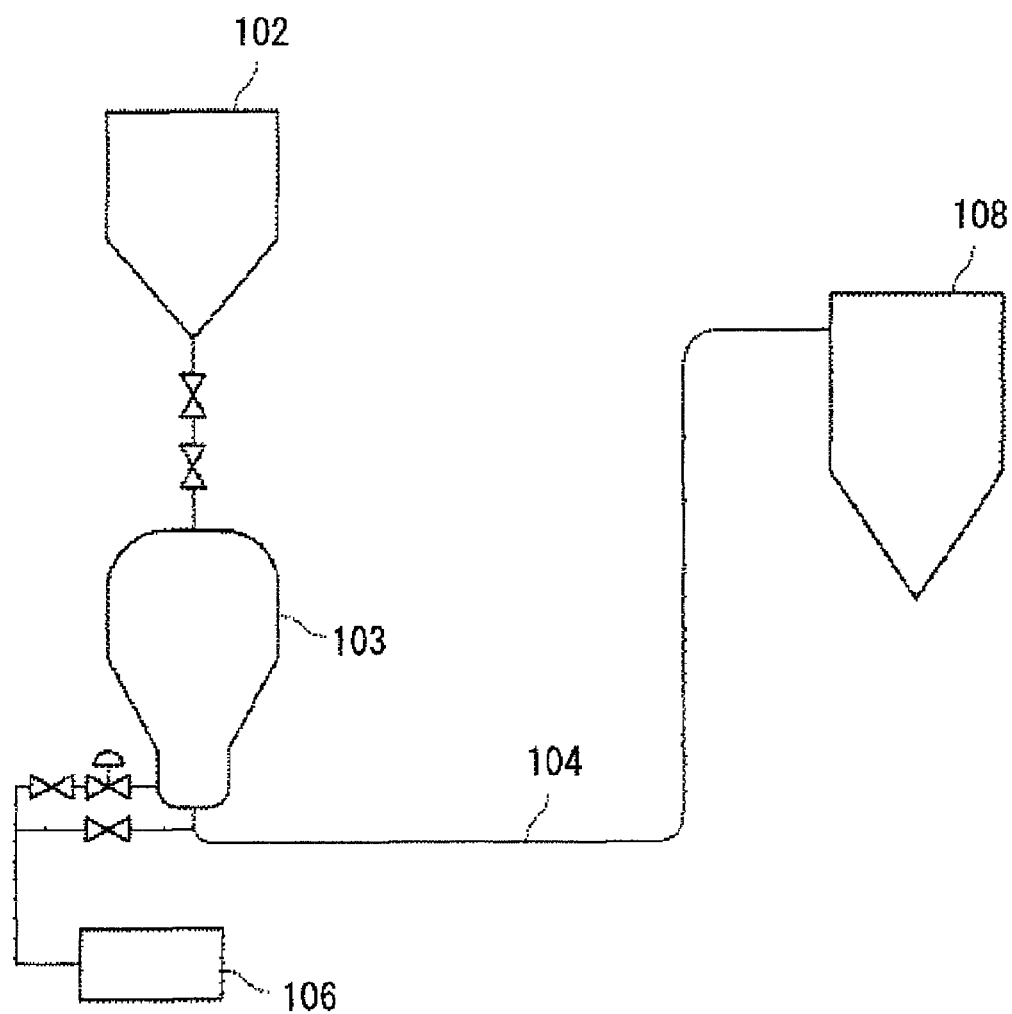

PARTICULATE WATER ABSORBING AGENT AND METHOD FOR PRODUCING THE SAME

This application is the U.S. national phase of International Application No. PCT/JP2008/056168, filed 28 Mar. 2008, which designated the U.S. and claims priority to Japanese Patent Application No. 2007-089601, filed 29 Mar. 2007 the entire contents of each of which are hereby incorporated by reference.

TECHNICAL FIELD

The present invention relates to a particulate water absorbing agent containing a water absorbent resin as a main component and a method for producing the same. More particularly, the present invention relates to a particulate water absorbing agent and a method for producing the same, the particulate water absorbing agent having: excellent powder properties (such as fluidity both when the agent is dry and when the agent has absorbed moisture and stability in its bulk density) without sacrificing water absorbing performance, thereby attaining stable absorbing properties, the particulate water absorbing agent causing not much re-wet and exhibiting excellent absorbing properties when used in an absorbent core of a sanitary material such as a disposable diaper, a sanitary napkin, and an incontinence pad.

BACKGROUND ART

Recently, water absorbent resins are widely used as a main constituent ingredient of a sanitary material (absorbing article) such as a disposable diaper, a sanitary napkin, and an incontinence pad so as to absorb body fluids (e.g., urine and blood). Examples of known water absorbent resins encompass: a partially neutralized cross-linked polymer of polyacrylic acid; a hydrolyzed starch-acrylonitrile graft polymer; a neutralized starch-acrylic acid graft polymer; a saponified vinyl acetate-acrylic ester copolymer; a cross-linked carboxymethyl cellulose; a hydrolyzed or cross-linked acrylnitryl copolymer or acrylamide copolymer; a cross-linked cationic monomer; a cross-linked isobutylene-maleic copolymer; and a cross-linked polymer of 2-acrylamide-2-methylpropanesulfonate and acrylic acid.

It has conventionally been desirable that the above water absorbent resins have such water absorbing properties as: a high absorption capacity for aqueous liquids including body fluids, particularly a high water absorption capacity under load; a high absorbing rate; an excellent liquid permeability; a high gel strength of a swelling gel thereof; and a high water absorption capacity to absorb water from a substrate in which an aqueous solution is contained.

For achievement of the above water absorbing properties, the above water absorbent resins are each a hydrophilic resin having a uniform cross-linked structure inside the polymer, thereby being insoluble in water. The water absorbent resins normally have particles having a surface cross-linked by, e.g., a cross-linking agent so that the particles have a gradient cross-linking density. This aims to improve each of the water absorbent resins in its water absorption rate, prevention of generation of fish eyes, gel strength, absorption capacity under pressure, prevention of gel blocking, and liquid permeability (see Patent Literatures 1 through 6).

For improvement of its water absorbing performance, for example, a particulate water absorbing agent is known that contains a water absorbent resin having particles having been subjected to a surface cross-linking treatment in the vicinity of the surface so as to have a gradient cross-linking density (Conventional Example 1).

In addition to the above water absorbing agent, a water absorbing agent is known that contains a water absorbent resin and metal soap so as to, e.g., improve its liquid permeability. Also, it is desired that a particulate water absorbing agent be available that not only has high water absorbing performance, but also has no mater whether it is dry or moist, a good powder fluidity and little adhesion to devices etc. during its production and transportation, and during production of an absorbent core from the water absorbent resin and a fiber material. To achieve a good powder fluidity when particulate water absorbing agents have absorbed moisture, addition of inorganic substance powder such as amorphous silicon dioxide or kaolin has been proposed. Known examples of particulate water absorbing agents containing inorganic substance powder encompass: a particulate water absorbing agent including inorganic substance powder and water absorbent resin powder; and a particulate water absorbing agent including stearic acid and inorganic substance powder (Conventional Example 2).

Other known examples encompass: a particulate water absorbing agent containing quaternary ammonium salt; a particulate water absorbing agent containing denatured polysiloxane as well as polyethylene glycol or polypropylene glycol; and a particulate water absorbing agent containing a polymeric dispersant (Conventional Example 3).

Still another known example is a particulate water absorbing agent containing a water absorbent resin having been treated with a surface active agent so as to prevent generation of fish eyes and gel blocking (Conventional Example 4).

Furthermore, a method for improving bulk density has also been proposed. For example, polishing cross-linked polymer particles and then carrying out surface cross-linking with respect to the particles allows for production of irregularly pulverized-shape water absorbent resin powder having a high bulk density and a high absorption capacity under pressure (Conventional Example 5).

Patent Literature 1, for example, discloses a particulate water absorbing agent produced by adding a surface cross-linking agent to a water absorbent resin having a cross-linked structure for surface cross-linking treatment and then adding a surface active agent or a powdered lubricant to the resin. Further, Patent Literature 2 discloses a superabsorbent polymer containing a monomer having a polymerizable, unsaturated acid group, an internal cross-linking agent, a surface cross-linking agent, a permeable modifier, polyhydric metal salt, a surface active agent, and insoluble inorganic powder. Another known water absorbing agent contains a water absorbent resin cross-linked or covered by a surface cross-linking agent in the vicinity of its surface, the water absorbent resin containing polyhydric metal salt and water-insoluble inorganic particles at least in its surface or in the vicinity of the surface.

CITATION LIST

Patent Literature 1
PCT International publication No. 2005/075070 pamphlet (Publication Date: Aug. 18, 2005)
Patent Literature 2
Japanese Translation of PCT International Application, Tokuhyo, No. 2006-526691 (Publication Date: Nov. 24, 2006)

Patent Literature 3

Japanese Translation of PCT International Application, Tokuhyohei, No. 8-509522 (Publication Date: Oct. 8, 1996)

Patent Literature 4

Japanese Translation of PCT International Application, Tokuhyo, No. 2004-512165 (Publication Date: Apr. 22, 2004)

Patent Literature 5

Chinese Patent Application Publication, No. 1970586 (Publication Date: May 30, 2007)

Patent Literature 6

Taiwanese Patent Application Publication, No. 200720346

SUMMARY OF INVENTION

The above water absorbing agents, however, each pose such problems that the water absorbing agent shows an insufficient powder fluidity obtained both when the agent is dry and when the agent is moist; that the water absorbing agent is significantly decreased in absorbing performance under load; or that a surface tension of a liquid to be absorbed such as urine, is decreased when the water absorbent resin is in contact with the liquid.

The particulate water absorbing agent of Conventional Example 1, for example, has a insufficiently low fluidity when it is dry and when it is moist. This causes a problem of poor usability of the water absorbent resin.

By the inorganic substance added therein, the particulate water absorbing agent of Conventional Example 2 indeed shows an improved fluidity when it is moist. However, when it is dry, the particulate water absorbing agent is significantly poor in fluidity and absorbing performance, whereby the water absorbent resin has poor handling property Besides, absorbing articles containing the above particulate water absorbing agent do not exhibit sufficient water absorbing properties. In particular, in case where a large amount of metal soap is added to the water absorbent resin, the absorbing performance of the water absorbent resin is adversely affected by properties of the metal soap such as hydrophobicity, water repellency, and surface activity.

The particulate water absorbing agent of Conventional Example 3 has an insufficient fluidity when it is moist. Further, when its water absorbent resin is in contact with a liquid to be absorbed such as urine, the liquid problematically has a decreased surface tension. This leads to deterioration in water absorbing properties of an absorbing article containing the particulate water absorbing agent; for example, use of the particulate water absorbing agent in a disposable diaper increases re-wet. Thus, the particulate water absorbing agent is not sufficiently useful.

The particulate water absorbing agent of Conventional Example 4 requires a large amount of a surface active agent to be used for its water absorbent resin and is therefore uneconomical. Further, when the particulate water absorbing agent is in contact with a liquid to be absorbed such as urine, the liquid has a decreased surface tension. This adversely affects absorbing performance of the particulate water absorbing agent; for example, use of the particulate water absorbing agent in a disposable diaper increases re-wet.

The irregularly pulverized-shape water absorbent resin powder of Conventional Example 5 has a high bulk density and thus has a good absorption capacity under load. However, achievement of this requires polishing the surface of the cross-linked polymer and thus requires more steps to produce the powder. In addition, this necessitates removing fine powder produced by the polishing of the surface of the cross-linked polymer and thus problematically increases a cost and complicates production.

The particulate water absorbing agent of Patent Literature 1 does not contain a liquid permeability improving agent such as polyhydric metal salt and thus problematically has a low liquid permeability.

Further, according to the superabsorbent polymer of Patent Literature 2, the surface cross-linking agent and the surface active agent are added concurrently, or the surface active agent is added immediately before or after addition of the surface cross-linking agent. This causes the later-added polyhydric metal salt to be precipitated on the surface of the polymer and as a result increases friction resistance of the superabsorbent polymer in powder form. This problematically leads to decrease in properties such as fluidity and damage resistance after pneumatic transportation.

Also, according to the water absorbing agent that contains a water absorbent resin cross-linked or covered by a surface cross-linking agent in the vicinity of its surface and further contains polyhydric metal salt and water-insoluble inorganic particles in the vicinity of the surface, the polyhydric metal salt is precipitated on the surface of the water absorbent resin. It has been found that this problematically leads to decrease in properties such as fluidity and damage resistance after pneumatic transportation.

Systems of pneumatic transportation are roughly grouped into two types: low-density pneumatic transportation and high-density pneumatic transportation. Specifically, the low-density pneumatic transportation allows transport of powder, i.e., an object to be transported, through a pneumatic tube in dispersed form. In contrast, the high-density pneumatic transportation allows transport of powder, i.e., an object to be transported, through a pneumatic tube in the form of lumps referred to as slag or a plug. Since maintaining powder in dispersed form requires a high airflow-down speed, the low-density pneumatic transportation is a high-speed transport. In contrast, the high-density pneumatic transportation is a low-speed transport. In general pneumatic transportation, blockage of a pneumatic tube is prevented by, e.g., increasing an amount of air for transport. However, this method causes increase in, e.g., transport pressure and transport speed and thus damages powder, i.e., an object to be transported, thereby problematically deteriorating properties of the powder. On the other hand, decreasing the amount of air for transport for alleviation of such damage leads to blockage of the pneumatic tube and thus problematically prevents stable pneumatic transportation. Therefore, achieving both maintenance of properties of an object to be transported and stable pneumatic transportation is a common objective.

The above Patent Literatures indeed allow achievement of a certain advantage (e.g., improvement in liquid permeability) on batch-wise production or in experiments in laboratory. However, the Patent Literatures do not always allow high properties in actual production. The inventors of the present invention have researched the cause of this and consequently found that the cause is unexpectedly the transport step.

More specifically, the inventors of the present invention have found problems peculiar to: particulate water absorbing agents containing a liquid permeability improving agent such as polyhydric metal salt and water-insoluble inorganic fine powder; and a method for producing such particulate water absorbing agents. Specifically, the problems are: decreased transportability (decreased productivity) due to use of a liquid permeability improving agent; and decreased properties due to transportation after mixing with the liquid permeability improving agent. The inventors have further found that, while a process of producing water absorbent resins involves use of many various conveyors (e.g., belt conveyor, screw conveyor, bucket conveyor, spring conveyor) that intermediately connect different steps, decrease in transportability and properties, the decrease being caused by the use of a liquid permeability improving agent, is significant in and peculiar to pneumatic transportation in comparison with other means.

The present invention has been accomplished in view of the above conventional problems. It is an object of the present invention to provide a particulate water absorbing agent and a method for producing the same, the particulate water absorbing agent having a superior pneumatic transportation status, maintaining an effect of a liquid permeability improving agent, and excelling in properties such as fluidity and damage resistance after pneumatic transportation.

In order to solve the above problems, a method for producing a particulate water absorbing agent in accordance with the present invention includes the steps of: adding an organic surface cross-linking agent to a water absorbent resin having a cross-linked structure; adding a liquid permeability improving agent to the water absorbent resin concurrently with or after the step of adding the organic surface cross-linking agent; and adding a lubrication improving agent to the water absorbent resin after the step of adding the liquid permeability improving agent.

The method for producing a particulate water absorbing agent in accordance with the present invention includes the steps of adding an organic surface cross-linking agent and a liquid permeability improving agent to a water absorbent resin having a cross-linked structure, followed by adding a lubrication improving agent to the water absorbent resin. Thus, a particulate water absorbing agent produced by the method for producing a particulate water absorbing agent in accordance with the present invention includes a lubrication improving agent layer as its outermost layer, i.e., farthest away from the water absorbent resin. This improves fluidity exhibited both when the particulate water absorbing agent has absorbed moisture and when it is dry. This in turn facilitates handling the particulate water absorbing agent during its transportation and also reduces adherence of the particulate water absorbing agent to, e.g., devices in use.

According to the method for producing a particulate water absorbing agent in accordance with the present invention, the liquid permeability improving agent is added to the water absorbent resin having a cross-linked structure. This improves liquid permeability of the particulate water absorbing agent thus produced by the method for producing a particulate water absorbing agent in accordance with the present invention. Thus, according to the above particulate water absorbing agent, decrease in the saline flow conductivity (SFC) due to the pneumatic transportation is small. The particulate water absorbing agent is also excellent in damage resistance.

The method for producing a particulate water absorbing agent in accordance with the present invention may preferably further include the step of pneumatically transporting the particulate water absorbing agent.

The pneumatic transportation does pose the above problems. However, the systems of pneumatic transportation are easy to maintain and are, due to the single transport path, also easy to install, in comparison with mechanical transporters such as conveyors. Therefore, such systems are preferentially used in the production of particulate water-holding agents. The above problems of damaging an object to be transported or of blocking the pneumatic tube are preventable by the art of the present invention. Therefore, pneumatic transportation can be a suitable transportation means in the production of water absorbing agents.

The method for producing a particulate water absorbing agent in accordance with the present invention may prefer-ably be arranged such that the step of adding the liquid permeability improving agent is carried out after the step of adding the organic surface cross-linking agent.

This provides a liquid permeability improving agent layer on an outer surface of the surface cross-linked layer included in the particulate water absorbing agent produced by the method for producing a particulate water absorbing agent in accordance with the present invention. The particulate water absorbing agent thus has a more excellent liquid permeability. Consequently, according to the above particulate water absorbing agent, decrease in the saline flow conductivity (SFC) due to the pneumatic transportation is smaller. The particulate water absorbing agent is also more excellent in damage resistance.

The method for producing a particulate water absorbing agent in accordance with the present invention may preferably be arranged such that the liquid permeability improving agent includes a polymeric polyamine compound, water-insoluble fine powder, or water-soluble polyhydric metal salt. Further, the method for producing a particulate water absorbing agent in accordance with the present invention may preferably be arranged such that the lubrication improving agent includes a surface active agent or a powdered lubricant.

This specifies a substance(s) for the liquid permeability improving agent and/or the lubrication improving agent used in the method for producing a particulate water absorbing agent in accordance with the present invention. Thus, the particulate water absorbing agent produced by the method for producing a particulate water absorbing agent in accordance with the present invention reliably excels in liquid permeability as well as fluidity exhibited both when the particulate water absorbing agent has absorbed moisture and when it is dry.

The method for producing a particulate water absorbing agent in accordance with the present invention may preferably be arranged such that the liquid permeability improving agent is added in a form of an aqueous solution or an aqueous dispersion solution.

According to the method for producing a particulate water absorbing agent in accordance with the present invention, the liquid permeability improving agent is preferably added in the form of an aqueous solution or an aqueous dispersion solution. This is because, e.g., the liquid permeability improving agent in the above form is easier to handle, has a better mixing property with respect to the particulate water absorbing agent, is less likely to be segregated after the mixing, and is more controllable so as not to be separated.

The method for producing a particulate water absorbing agent in accordance with the present invention may preferably further include the steps of a thermal surface cross-linking step and a cooling step, wherein: the thermal surface cross-linking step includes the step of adding organic surface cross-linking agent to the water absorbent resin and performing a surface cross-linking treatment; and concurrently with or after the cooling step, the step of adding the liquid permeability improving agent and the step of adding the lubrication improving agent are performed in this successive order.

The method for producing a particulate water absorbing agent in accordance with the present invention, the method being arranged as above, allows for efficient production of particulate water absorbing agents excelling in properties such as fluidity and damage resistance after the pneumatic transportation.

The method for producing a particulate water absorbing agent in accordance with the present invention may preferably be arranged such that the water absorbent resin has a centrifuge retention capacity (CRC) of not less than 10 g/g and not more than 60 g/g.

This provides a superior absorbent property to particulate water absorbing agents produced by the method for producing a particulate water absorbing agent in accordance with the present invention.

The method for producing a particulate water absorbing agent in accordance with the present invention may preferably be arranged such that the water absorbent resin has a mass median particle size (D50) of not less than 150 μm and less than 850 μm.

According to the above method for producing a particulate water absorbing agent in accordance with the present invention, the particulate water absorbing agent thus produced does not have too small a mass median particle size. This causes no dust at handling the particulate water absorbing agent and thus prevents deterioration of the working environment. In addition, the above particulate water absorbing agent does not have too large a mass median particle size. This does not slow a water absorption rate of the particulate water absorbing agent. Further, the particulate water absorbing agent, when used in an absorbing article, does not deteriorate a texture of the absorbing article, and thus does not cause a user to feel uncomfortable.

The method for producing a particulate water absorbing agent in accordance with the present invention may preferably be arranged such that the water absorbent resin has an absorbency against pressure (AAP) under 4.83 kPa, the AAP being not less than 20 g/g and not more than 40 g/g, during a period between the step of adding the liquid permeability improving agent and the step of adding the lubrication improving agent.

This provides a superior absorbent property to particulate water absorbing agents produced by the method for producing a particulate water absorbing agent in accordance with the present invention. When the absorbency against pressure (AAP) of the water absorbent resin falls outside the above range, the particulate water absorbing agent, when used in, e.g., a diaper, may not unfavorably exhibit high properties.

A particulate water absorbing agent of the present invention includes on a surface of the water absorbent resin a portion including a surface cross-linked layer, a liquid permeability improving agent layer, and a lubrication improving agent layer.

The particulate water absorbing agent of the present invention, which includes a surface cross-linked layer, a liquid permeability improving agent layer, and a lubrication improving agent layer, achieves both liquid permeability and fluidity.

The particulate water absorbing agent of the present invention may preferably be arranged such that the particulate water absorbing agent has an absorbency against pressure (AAP) under 4.83 kPa, the AAP being not less than 20 g/g and not more than 40 g/g.

The particulate water absorbing agent of the present invention thus has an excellent absorbent property. When the absorbency against pressure (AAP) of the particulate water absorbing agent falls outside the above range, the particulate water absorbing agent, when used in, e.g., a diaper, may not unfavorably exhibit high properties.

The particulate water absorbing agent of the present invention may preferably be arranged such that the particulate water absorbing agent has a saline flow conductivity (SFC) of 10 ($10^{-7} \cdot cm^3 \cdot s \cdot g^{-1}$) or more.

This provides an excellent liquid permeability to the particulate water absorbing agent of the present invention.

A method for transporting a particulate water absorbing agent in accordance with the present invention is a method of transporting a particulate water absorbing agent including the organic surface cross-linking agent and a liquid permeability improving agent. The method may preferably include the steps of: further adding a lubrication improving agent to the particulate water absorbing agent; and pneumatically transporting the particulate water absorbing agent after the step of adding the lubrication improving agent. As mentioned above, the particulate water absorbing agent, which includes the organic surface cross-linking agent and the liquid permeability improving agent, may further include other components such as a lubrication improving agent.

In general pneumatic transportation, blockage of a transport tube is preventable, e.g., by increasing an amount of air for transportation. This method, however, increases transportation pressure, transportation speed and the like. This in turn damages an object to be transported and decreases its properties. On the other hand, decreasing the amount of air for transportation to alleviate the damage causes the blockage of a transport tube as described above. This prevents stable pneumatic transportation. In view of this, according to the method for transporting a particulate water absorbing agent in accordance with the present invention, a lubrication improving agent is added to the particulate water absorbing agent before the pneumatic transportation. The particulate water absorbing agent is thus pneumatically transported while having a lubrication improving agent layer on its surface. This eliminates the need to increase the amount of air for transportation to prevent the blockage of a transport tube. Consequently, the method for transporting a particulate water absorbing agent in accordance with the present invention achieves both maintenance of properties of the particulate water absorbing agent and stable pneumatic transportation of the particulate water absorbing agent.

The method for transporting a particulate water absorbing agent in accordance with the present invention may preferably further include the steps of: adding an organic surface cross-linking agent to a water absorbent resin having a cross-linked structure; and adding a liquid permeability improving agent to the water absorbent resin concurrently with or after the step of adding the organic surface cross-linking agent; further adding a lubrication improving agent to the particulate water absorbing agent; and pneumatically transporting the particulate water absorbing agent after the steps above.

According to the method for transporting a particulate water absorbing agent in accordance with the present invention, the particulate water absorbing agent is pneumatically transported while having on its surface a liquid permeability improving agent layer and a lubrication improving agent layer in this successive order from the water absorbent resin. Thus, a particulate water absorbing agent transported by the method for transporting a particulate water absorbing agent in accordance with the present invention has a more excellent liquid permeability. As a result, with regard to the above particulate water absorbing agent, decrease in the saline flow conductivity (SFC) due to the pneumatic transportation is even smaller. The particulate water absorbing agent has an even more excellent damage resistance.

The method for transporting a particulate water absorbing agent in accordance with the present invention may be arranged such that: the liquid permeability improving agent includes a polymeric polyamine compound, water-insoluble fine powder, or water-soluble polyhydric metal salt; and the lubrication improving agent includes a surface active agent.

This specifies respective substances for the liquid permeability improving agent and the lubrication improving agent used in the method for transporting a particulate water absorbing agent in accordance with the present invention. As a result, the particulate water absorbing agent transported by the method for transporting a particulate water absorbing agent in accordance with the present invention reliably excels in liquid permeability as well as fluidity exhibited both when the particulate water absorbing agent has absorbed moisture and when it is dry.

The method for transporting a particulate water absorbing agent in accordance with the present invention may be arranged such that the particulate water absorbing agent is transported over a transportation distance of not less than 10 m and not more than 1000 m.

According to the method for transporting a particulate water absorbing agent in accordance with the present invention, the particulate water absorbing agent includes the organic surface cross-linking agent and the liquid permeability improving agent. Thus, the particulate water absorbing agent excels in liquid permeability and fluidity, and is transportable over a long distance.

The method for transporting a particulate water absorbing agent in accordance with the present invention may be arranged such that the particulate water absorbing agent is continuously transported in an amount of not less than 1 metric ton/hr.

According to the method for transporting a particulate water absorbing agent in accordance with the present invention, the particulate water absorbing agent includes the organic surface cross-linking agent and the liquid permeability improving agent. Thus, the particulate water absorbing agent excels in liquid permeability and fluidity, and is continuously transportable in a large amount. In addition, according to the above method for transporting a particulate water absorbing agent in accordance with the present invention, the particulate water absorbing agent is continuously transported in an amount of not less than 1 metric ton/hr. The particulate water absorbing agent thus transported remarkably excels in liquid permeability and fluidity, as compared to particulate water absorbing agents transported by conventional methods for transporting a particulate water absorbing agent.

Additional objects, features, and strengths of the present invention will be made clear by the description below. Further, the advantages of the present invention will be evident from the following explanation in reference to the drawing.

BRIEF DESCRIPTION OF DRAWINGS

FIG. 1

FIG. 1 is a cross-sectional view illustrating an embodiment of a high-density pneumatic transportation device in accordance with the present invention.

REFERENCE SIGNS LIST

102 hopper
103 lift tank
104 transport tube
106 compressor
108 hopper

DESCRIPTION OF EMBODIMENTS

The following describes the present invention in detail. The scope of the invention is, however, not limited to the description below. The present invention may be put into practice in manners modified appropriately from those illustrated below, provided that such alteration is not a departure from the gist of the invention.

A particulate water absorbing agent of the present invention includes a water absorbent resin having a cross-linked structure, the water absorbent resin having a surface portion containing: an organic surface cross-linked layer; a layer of a liquid permeability improving agent; and a layer of a lubrication improving agent. The particulate water absorbing agent of the present invention preferably has the above surface portion formed by: adding an organic surface cross-linking agent to the water absorbent resin having a cross-linked structure for a surface cross-linking treatment; adding a liquid permeability improving agent to the water absorbent resin concurrently with or after the surface cross-linking treatment; and then adding a lubrication improving agent to the water absorbent resin. The particulate water absorbing agent of the present invention is preferably produced through a step of pneumatic transportation.

The particulate water absorbing agent may include a water absorbent resin having a cross-linked structure, the water absorbent resin only containing an organic surface cross-linking agent, a liquid permeability improving agent, and a lubrication improving agent. Alternatively, the water absorbent resin may also contain other materials, provided that they do not impair properties of the particulate water absorbing agent. A method for adding such other materials is not particularly limited.

The following describes in detail the water absorbent resin, the organic surface cross-linking agent, the liquid permeability improving agent, the lubrication improving agent, the particulate water absorbing agent, parameters for achieving, e.g., superior absorbing performance of the particulate water absorbing agent as well as excellent fluidity in its powder form, and a water absorbing article. Note that, in the present specification, "mass" is synonymous with "weight" and "grain diameter" is synonymous with "particle size."

The particulate water absorbing agent of the present invention is used to absorb water, various aqueous solutions, and other aqueous solutions such as urine and blood. The particulate water absorbing agent includes as a main component a water absorbent resin having a purity normally within a range from 70 to 100 weight % (mass %), preferably within a range from 80 to 100 weight %, or more preferably within a range from 90 to 100 weight % in relation to a solid content of the particulate water absorbing agent.

(I) Water Absorbent Resin

The present invention requires, as the water absorbent resin, a water absorbent resin obtained by cross-linking and polymerizing an unsaturated monomer containing an acid group and/or its salt (any water absorbent resin having a cross-linked structure may be used; alternatively, a water absorbent resin may be used that is obtained by the polymerization of the unsaturated monomer containing an acid group and/or its salt and then a cross-linking reaction based on either a cross-linking agent or self cross-linking at the time of polymerization).

The water absorbent resin of the present invention is a water-swelling and water-insoluble cross-linked polymer capable of forming hydrogel. A "water-swelling" water absorbent resin has a CRC (detailed later) to absorb a large amount of water, i.e., an amount at least not smaller than 5 times or preferably 50 to 1000 times its own weight in ion exchanged water or physiological saline. A "water-insoluble" water absorbent resin has an uncross-linked water-soluble content (water-soluble polymer) of the water absorbent resin, the uncross-linked water-soluble content being, in accordance with ERT 470.1-99, preferably not higher than 50 weight % (where the lower limit is 0%), more preferably not higher than 25 weight %, even more preferably not higher than 20 weight %, particularly preferably not higher than 15 weight %, or most preferably not higher than 10 weight %.

The cross-linked polymer is a polymer obtained by polymerization of an unsaturated monomer, the polymer internally having a cross-linked structure (hereinafter referred to as "internal cross-linked structure") in order to achieve a favorable absorbent property. Further, the water absorbent resin may be subjected to a surface cross-linking treatment to form a cross-linked structure in the vicinity of a surface of the water absorbent resin. To achieve an excellent absorbent property, the surface cross-linking treatment is preferably carried out.

Examples of the water absorbent resin including the cross-linked polymer encompass individual ones of or combinations of two or more of: a partially neutralized polyacrylic acid polymer; a hydrolyzed starch-acrylonitril graft polymer; a starch-acrylic acid graft polymer or its neutralized polymer; a cross-linked carboxymethyl cellulose; a saponified vinyl acetate-acrylic ester copolymer; a hydrolyzed or cross-linked acrylnitryl copolymer or acrylamide copolymer; a denatured cross-linked polyvinyl alcohol containing a carboxyl group; a cross-linked cationic monomer; a cross-linked polymer of 2-acrylamide-2-methylpropanesulfonate and acrylic acid; and a cross-linked isobutylene-maleic (anhydride) copolymer. Among the above, the water absorbent resin preferably includes a partially neutralized polyacrylic acid polymer obtained by polymerizing and cross-linking an unsaturated monomer containing acrylic acid and/or its salt (neutralized polymer) as a main component.

The water absorbent resin including the cross-linked polymer is obtained by polymerizing and cross-linking an unsaturated monomer and is subjected to the surface cross-linking treatment as necessary. The following explains an unsaturated monomer, a cross-linking monomer (internal cross-linking agent), and a polymerization initiator, all of which are used to produce the water absorbent resin. The following also explains a method for producing the water absorbent resin.

<Unsaturated Monomer>

Any unsaturated monomer can be used as the unsaturated monomer used to produce the water absorbent resin included in the particulate water absorbing agent of the present invention, provided that the unsaturated monomer allows obtaining a desired cross-linked polymer.

When the cross-linked polymer is, for example, a partially neutralized polyacrylic acid polymer, an acrylic acid and/or its salt (neutralized polymer) is/are used as a main component. Alternatively, an additional unsaturated monomer other than the acrylic acid and/or its salt may be used as a copolymer component along with the acrylic acid and/or its salt. This provides the resultant water absorbent resin with not only the absorbent property, but also other properties such as antibacterial and deodorant properties, and also allows for production of the water absorbent resin at a lower cost.

Examples of the additional unsaturated monomer encompass water-soluble or water-insoluble unsaturated monomers such as: acid-group monomers including β-acryloyl oxypropionic acid, methacrylic acid, maleic acid (anhydride), fumaric acid, crotonic acid, itaconic acid, vinyl sulfonate, 2-(meth)acrylamide-2-methylpropane sulfonate, and (meth) acryloxyalkane sulfonate, as well as alkali metal salt, ammonium salt, and alkylamine salt thereof; and N-vinyl-2-pyrrolidone, N-vinylacetamide, (meth)acrylamide, N-isopropyl (meth)acrylamide, N,N-dimethyl(meth)acrylamide, 2-hydroxyethyl(meth)acrylate, methoxypolyethyleneglycol (meth)acrylate, polyethyleneglycol(meth)acrylate, isobutylene, and lauryl(meth)acrylate. These unsaturated monomers may be used independently or in a suitable combination of two or more. The unsaturated monomer used in the present invention further encompasses a monomer containing the above unsaturated monomer as a copolymerization component.

Note that, when an unsaturated monomer containing an acid group is used as the unsaturated monomer and the additional unsaturated monomer, a salt of the unsaturated monomer may be a monovalent salt such as an alkali metal salt, an alkali earth metal salt, or an ammonium salt, and is preferably the alkali metal salt. Among the above, it is preferable to at least use sodium salt or potassium salt in view of performance of the resultant water absorbent resin and industrial easy availability and safety of such salt of the unsaturated monomer, for example.

When the acrylic acid (salt) is used in combination with another additional unsaturated monomer, such an additional unsaturated monomer is contained in an amount preferably within a range from 0 to 30 mol %, more preferably within a range from 0 to 10 mol %, or even more preferably within a range from 0 to 5 mol % in relation to a total number of moles in all the unsaturated monomers used to produce the water absorbent resin. Stated differently, the acrylic acid and its salt serving as a main component is/are simply required to have a number of moles preferably within a range from 70 to 100 mol %, more preferably within a range from 90 to 100 mol %, or even more preferably within a range from 95 to 100 mol % in relation to the total number of moles in all the unsaturated monomers used to produce the water absorbent resin.

The unsaturated monomer containing an acid group such as acrylic acid is preferably substantially neutral in view of its properties and pH. Further, the acid group is preferably neutralized. The acid group as a polymer has a neutralization ratio (mol % of a neutralized portion of the acid groups) generally within a range from 20 to 100 mol %, preferably within a range from 30 to 95 mol %, or more preferably within a range from 40 to 80 mol %. The acid group may be neutralized with a monomer, a polymer, or a combination of them.

<Cross-Linking Monomer (Internal Cross-Linking Agent)>

The water absorbent resin used in the present invention is a cross-liked polymer having an internal cross-linked structure. The water absorbent resin may be regarded as having an internal cross-linked structure, provided that the water absorbent resin has water-insolubility and water-swelling property. Thus, the internal cross-linked structure of the water absorbent resin may be obtained without using any cross-linking monomer serving as an internal cross-linking agent; it may be obtained by self cross-linking of the unsaturated monomer. However, the internal cross-linked structure is preferably obtained by copolymerizing or reacting the unsaturated monomer with the cross-linking monomer. The cross-linking monomer serving as an internal cross-linking agent refers to a monomer having in its single molecule either of two or more polymerizable unsaturated groups and two or more reactive groups.

Examples of the internal cross-linking agent encompass N,N'-methylene bis(meth)acrylamide, (poly)ethylene glycol di(meth)acrylate, (poly) propylene glycol di(meth)acrylate, trim ethylolpropane tri(meth)acrylate, glycerin tri(meth)acrylate, glycerin acrylate methacrylate, ethylene oxide denatured trimethylolpropane tri(meth)acrylate, pentaerythritol hexa(meth)acrylate, triallyl cyanurate, triallyl isocyanurate, triallyl phosphate, triallyl amine, poly(meth)allyloxyalkane, (poly) ethylene glycol diglycidyl ether, glycerol diglycidyl ether, ethylene glycol, polyethylene glycol, propylene glycol, glycerine, pentaerythritol, ethylenediamine, ethylenecarbonate, propylenecarbonate, polyethylene imine, and glycidyl (meth)acrylate.

These internal cross-linking agents may be used independently, or two or more of them may be used in combination as appropriate. Further, the internal cross-linking agent may be added to a reaction system at one time or in separate portions. When at least either one kind or two or more of the internal cross-linking agents are used, it is preferable to use at least a cross-linking monomer having two or more polymerizable unsaturated groups at the time of polymerization, in view of, e.g., the absorbent property of the resultant particulate water absorbing agent.

To achieve a favorable property of the water absorbent resin, the internal cross-linking agent is contained in an amount preferably within a range from 0.001 to 2 mol %, more preferably within a range from 0.005 to 0.5 mol %, further preferably within a range from 0.01 to 0.2 mol %, or particularly preferably within a range from 0.03 to 0.15 mol % in relation to the total number of moles in the unsaturated monomer (except the cross-linking agent) used to produce the water absorbent resin. The amount of the internal cross-linking agent to be used being smaller than 0.001 mol % or larger than 2 mol % is not preferable because the resultant water absorbent resin may not have a sufficient absorbent property.

When the cross-linked structure is introduced into a polymer by using the internal cross-linking agent, the internal cross-linking agent may be added to the reaction system before, during, or after the polymerization of the unsaturated monomer, or after the neutralization.

<Polymerization Initiator>

The polymerization of the unsaturated monomer for producing the water absorbent resin used, in the present invention preferably involves use of a polymerization initiator. Examples of such a polymerization initiator encompass: a radical polymerization initiator such as potassium persulfate, ammonium persulfate, sodium persulfate, potassium peracetate, sodium peracetate, potassium percarbonate, sodium percarbonate, t-butyl hydroperoxide, and hydrogen peroxide, 2,2'-azobis (2-amidino propane) dihydrochloride; and a photo polymerization initiator such as 2-hydroxy-2-methyl-1-phenyl-propane-1-one.

In view of the physical property of the water absorbent resin, the polymerization initiator is contained in an amount preferably within a range from 0.001 to 2 mol %, or more preferably within a range from 0.01 to 0.1 mol % in relation to the total number of moles in the entire unsaturated monomer used to produce the water absorbent resin. The amount of the polymerization initiator being less than 0.001 mol % is not preferable because such an amount leads to a larger amount of an unreacted unsaturated monomer. On the other hand, the amount of the polymerization initiator being larger than 2 mol % is also not preferable because such an amount impedes control of the polymerization.

<Polymerization Method>

To produce the water absorbent resin used in the present invention, each of the above monomers (the unsaturated monomer, the additional unsaturated monomer, the cross-linking monomer) may be polymerized by, e.g., aqueous solution polymerization, reversed phase suspension polymerization, bulk polymerization, or precipitation polymerization. In consideration of performance of the resultant water absorbent resin, ease control of the polymerization, and the absorbent property of a swelling gel, preferable polymerization methods among the above are aqueous polymerization and reversed phase suspension polymerization, both of which use the monomers in a form of an aqueous solution. A fuller advantage of the present invention is achieved by aqueous polymerization, preferably by kneader polymerization or belt polymerization, or more preferably by continuous kneader polymerization or continuous belt polymerization.

When the monomers are each polymerized in the form of an aqueous solution, the aqueous solution (hereinafter referred to as "monomer aqueous solution") contains the monomer in a concentration depending on a temperature of the solution and a type of the monomer. Thus, the concentration is not particularly limited. However, the concentration is generally within a range from 10 to 80 weight %, preferably within a range from 10 to 70 weight %, or more preferably within a range from 20 to 60 weight %. Further, the aqueous solution polymerization may also involve a solvent other than water as necessary. A type of such a solvent to be used is not particularly limited.

The polymerization of the monomer may be initiated with use of the above polymerization initiator. Besides the polymerization initiator, an activating energy ray such as an ultraviolet ray, an electron ray, and a γ ray, may be used solely or in combination with the polymerization initiator. The monomer is polymerized at temperatures preferably within a range from 15 to 130° C., or more preferably within a range from 20 to 120° C., the temperatures depending on the type of the polymerization initiator to be used. Temperatures outside the above range during the polymerization may increase an amount of a residual monomer in the resultant water absorbent resin and/or cause excessive self cross-linkage. This undesirably decreases the absorbent property of the water absorbent resin.

The reversed phase suspension polymerization is a polymerization method in which the monomer aqueous solution is suspended in a hydrophobic organic solvent in a form of particles. The reversed phase suspension polymerization is described in documents such as U.S. Pat. Nos. 4,093,776, 4,367,323, 4,446,261, 4,683,274, and 5,244,735.

The aqueous solution polymerization is a polymerization method in which the monomer aqueous solution is polymerized without use of a dispersion solvent. The aqueous solution polymerization is described in documents such as U.S. Pat. Nos. 4,625,001, 4,873,299, 4,286,082, 4,973,632, 4,985,518, 5,124,416, 5,250,640, 5,264,495, 5,145,906, and 5,380,808, as well as European Patents Nos. 0,811,636, 0,955,086, and 0,922,717. The monomers and the polymerization initiators disclosed as examples in the above U.S. and European Patents may also be used in the present invention.

<Drying>

Polymerizing the monomer by the above methods generally yields a cross-linked polymer hydrogel, which is then dried and crushed as necessary. The cross-linked polymer hydrogel is generally crushed before and/or after being dried.

The cross-linked polymer hydrogel is dried by a method not particularly limited, and thus may be dried by various methods allowing a target moisture content to be attained, the methods encompassing heating, hot air drying, drying under reduced pressure, infrared drying, microwave drying, drying by azeotropy with a hydrophobic organic solvent, and high humidity drying involving use of high temperature steam. The hot-air drying uses hot air generally within a range from 60 to 250° C., preferably within a range from 100 to 220° C., or more preferably within a range from 120 to 200° C. The polymer is dried for a period selected according to a surface area and a moisture content of the polymer and a kind of the dryer so that the polymer has a target moisture content. The polymer is dried, e.g., for a period selected as appropriate from a range from 1 minute to 5 hours.

The moisture content of the water absorbent resin usable in the present invention is not particularly limited (the term "moisture content" is defined by an amount of water contained in the water absorbent resin and the particulate water absorbing agent; the content is represented by a proportion of an amount of the water absorbent resin, the amount being lost when the water absorbent resin is dried at 180° C. for 3 hours, to the amount of the water absorbent resin before it is dried). However, to achieve a favorable property of the particulate water absorbing agent of the present invention including the water absorbent resin as a main component, the water absorbent resin preferably has a moisture content allowing for control of the water absorbent resin so that it is in the form of particles (powder) exhibiting fluidity even at room temperature. Specifically, the particulate water absorbing agent is preferably in the form of powder having a moisture content within a range from 0 to 30 weight % (the moisture content being defined by the amount of the particulate water absorbing agent, the amount being lost when 1 g of the particulate water absorbing agent is stood and dried at 180° C. for 3 hours), more preferably within a range from 0.2 to 30 weight %, even more preferably within a range from 0 to 20 weight %, yet more preferably within a range from 0.3 to 15 weight %, or particularly preferably within a range from 0.5 to 10 weight %. The cross-linked polymer hydrogel is dried to produce a water absorbent resin in order to obtain a particulate water absorbing agent having a moisture content that falls within the above ranges. However, a high moisture content results in a low fluidity. This impedes production of the water absorbent resin and additionally prevents the water absorbent resin from being crushed. This in turn prevents the water absorbent resin from being controlled so that it has a particular particle size distribution.

When the above monomer is polymerized by reversed phase suspension polymerization, the cross-linked polymer hydrogel obtained when the polymerization reaction ends may be dried as follows: The cross-linked polymer hydrogel is dispersed in an organic solvent of a hydrocarbon such as hexane and azeotropically dried so as to have a moisture content of 40 weight % or less (where the lower limit is 0 weight %; preferably not less than 5 weight %), or preferably 30 weight % or less. After that, the cross-linked polymer hydrogel is separated by decantation or volatilization from the organic solvent and is then dried as necessary. The water absorbent resin of the present invention may be provided with, e.g., an organic surface cross-linking agent, a liquid permeability improving agent, and a lubrication improving agent (all of which are described later) to be mixed during or after the polymerization. When added to be mixed after the polymerization, the above are added before, during, or after the crushing.

(II) Organic Surface Cross-Linking Agent

The water absorbent resin used in the particulate water absorbing agent of the present invention is, as described above, cross-linked, polymerized, dried, and, as necessary, crushed. The water absorbent resin is further subjected to an organic surface cross-linking treatment (secondary cross-linking treatment) in the vicinity of its surface. An organic surface cross-linking agent is normally cross-linked with the water absorbent resin through covalent bonding and surface polymerization. Note that the water absorbent resin of the present invention may not be subjected to a surface cross-linking treatment.

The water absorbent resin may be cross-linked in the vicinity of its surface with use of various organic surface cross-linking agents. Thus, the organic surface cross-linking agent to be used is not particularly limited. However, the organic surface cross-linking agent is preferably a compound containing two or more functional groups reactive to functional groups of the water absorbent resin. To improve the absorbing performance of the water absorbent resin, the organic surface cross-linking agent is normally, for example, a polyhydric alcohol compound; an epoxy compound; a polyepoxy compound; a polyhydric amine compound or its condensate with a haloepoxy compound; an oxazoline compound; a mono, di, or polyoxazolidinone compound; or an alkylenecarbonate compound. Among the above, one that is reactive to a carboxyl group of the water absorbent resin through dehydration cross-linking is preferable; specifically, a hydroxyl group, an amino group, and their derivatives (a hydroxyl group formed by ring-opening of, e.g., alkylene carbonate or oxazolidinone) are preferable.

Specific examples of the organic surface cross-linking agent usable in the present invention are described in U.S. Pat. Nos. 6,228,930, 6,071,976, and 6,254,990. Such specific examples encompass: polyhydric alcohol compounds such as mono, di, tri, tetra, polyethyleneglycol, monopropyleneglycol, 1,3-propanediol, dipropyleneglycol, 2,3,4-trimethyl-1,3-pentandiol, polypropyleneglycol, glycerin, polyglycerin, 2-butene-1,4-diol, 1,4-butandiol, 1,3-butandiol, 1,5-pentandiol, 1,6-hexanediol, 1,2-cyclohexanedimethanol, and sorbitol; epoxy compounds such as ethyleneglycol diglycidyl ether and glycidol; polyhydric amine compounds such as ethylenediamine, diethylenetriamine, triethylenetetramine, tetraethylenepentamine, pentaethylenehexamine, polyethyleneimine, and polyamidepolyamine; haloepoxy compounds such as epichlorohydrin, epibromhydrin, and α-methyl epichlorohydrin; condensates of the polyhydric amine compound and the haloepoxy compound; oxazolidinone compounds such as 2-oxazolidinone; alkylene carbonate compounds such as ethylenecarbonate. The surface cross-linking agent is, however, not particularly limited.

The above organic surface cross-linking agents may be used solely, or two or more of them may be mixed for use as appropriate. To maximize the advantage of the present invention, it is preferable to at least use a dehydration cross-linking agent, particularly a polyhydric alcohol, among the above cross-linking agents. The polyhydric alcohol preferably has 2 to 10 carbon atoms or more preferably has 3 to 8 carbon atoms in its molecule.

The organic surface cross-linking agent is used in an amount determined depending on a compound to be used or a combination of such compounds. However, in relation to 100 parts by weight (mass) of the water absorbent resin, the surface cross-linking agent is contained in an amount preferably within a range from 0.001 to 10 parts by weight, or more preferably within a range from 0.01 to 5 parts by weight.

The surface cross-linking treatment preferably involves use of water. Such water is used in an amount determined depending on the moisture content of the water absorbent resin to be used. The water is used in an amount preferably within a range from 0.5 to 20 parts by weight, or more preferably within a range from 0.5 to 10 parts by weight, in relation to 100 parts by weight of the water absorbent resin.

Further, the surface cross-linking treatment may involve use of a hydrophilic organic solvent or a mix solvent of water and an hydrophilic organic solvent, instead of water. The hydrophilic organic solvent or the mixed solvent is used in an amount within a range from 0 to 10 parts by weight, preferably within a range from 0 to 5 parts by weight, or more preferably within a range from 0 to 3 parts by weight, in relation to 100 parts by weight of the water absorbent resin.

The organic surface cross-linking agent may be added by various methods. However, it is preferable to adopt a method in which the organic surface cross-linking agent is mixed beforehand with water and/or a hydrophilic organic solvent as necessary and then is sprayed or dropped onto the water absorbent resin. Spraying the organic surface cross-linking agent onto the water absorbent resin is more preferable. In case where the organic surface cross-linking agent is sprayed onto the water absorbent resin, the sprayed droplets have an average diameter preferably in a range from 0.1 to 300 µm, or more preferably in a range from 0.1 to 200 µm.

The water absorbent resin, the organic surface cross-linking agent, and water or a hydrophilic organic solvent are mixed together with a mixer preferably having a great mixing power to ensure even mixture of the above. Preferably examples of the mixer encompass a cylindrical mixer, a double-wall conical mixer, a high-speed stirring mixer, a V-shaped mixer, a ribbon-type mixer, a screw-type mixer, a double-arm kneader, a grinding kneader, a rotary mixer, an air-flow-type mixer, a Turbulizer, a batch-type Lodige mixer, and a continuous Lodige mixer.

When the organic surface cross-linking agent is mixed with the other ingredients to produce the particulate water absorbing agent of the present invention, the organic surface cross-linking agent may be mixed, before the surface cross-linking, with a polymeric additive having as a side chain a hydrocarbon group containing 7 or more carbon atoms, or coexist with such a polymeric additive. Further, the organic surface cross-linking agent, when mixed with the other ingredients, may coexist with water-insoluble fine powder, provided that such coexistence does not impair the advantage of the present invention.

After mixed with the organic surface cross-linking agent, the water absorbent resin is preferably subjected to a heating treatment. The water absorbent resin is heated at temperatures (of the water absorbent or a heating medium) generally within a range from 80 to 300° C., preferably within a range from 100 to 250° C., more preferably within a range from 150 to 250° C., or even more preferably within a range from 180 to 240° C. Also, the water absorbent resin is heated for a duration within a range from 1 minute to 2 hours. The water absorbent resin is preferably heated, e.g., at 180° C. for 0.1 to 1.5 hours, or at 200° C. for 0.1 to 1 hour.

When the water absorbent resin is produced by reverse phase suspension polymerization, the organic surface cross-linking agent is dispersed in a hydrophobic organic solvent used in reverse phase suspension polymerization and is heated for azeotropic dehydration, during and/or after the post-polymerization azeotropic dehydration. The resultant cross-linked polymer in a hydrogel form has a moisture content of 50 weight % or lower, preferably 40 weight % or lower, or more preferably 30 weight %, for example. This produces a water absorbent resin having a cross-linked surface.

Another mode of the surface cross-linking treatment of the present invention is as follows: A treatment solution containing a radically polymerizable compound is added as an organic surface cross-linking agent to the water absorbent resin and the resultant mixture is irradiated with an activating energy ray. The mode is disclosed, e.g., in U.S. Patent Application Publication No. 2005/0048221 (priority claimed on Japanese Patent Application (Tokugan) No. 2003-303306) and WO2006/062253. Alternatively, a surface active agent may be added to the above treatment solution. This treatment solution is added to the water absorbent resin and the resultant mixture is irradiated with an activating energy ray for a surface cross-linking treatment. A further alternative mode of the surface cross-linking treatment of the present invention is as follows: an aqueous solution containing a peroxide radical initiator is added to the water absorbent resin and the resultant mixture is heated. The mode is disclosed, e.g., in Japanese Examined Patent Publication (Kokoku) No. 7-8883.

The water absorbent resin of the present invention being subjected to a surface cross-linking treatment as described above preferably has a particular particle size (particle size) adjusted so that the water absorbent resin has a high fluidity when it is moist and a high bulk density. The particle size of the water absorbent resin, which also applies to a particle size of the later-described particulate water absorbing agent, is not described in detail here. The particle size of the water absorbent resin and the particulate water absorbing agent may be adjusted by adding/mixing insoluble particles or hydrophilic solvent, preferably water, and by further carrying out agglomeration, in accordance with the object and necessity.

(III) Liquid Permeability Improving Agent

According to the particulate water absorbing agent of the present invention, a liquid permeability improving agent in addition to the organic surface cross-linking agent is added to the water absorbent resin concurrently with or after the addition of the organic surface cross-linking agent. The liquid permeability improving agent used in the present invention refers to a material that is added to the water absorbent resin particles that may have a cross-linked surface. The liquid permeability improving agent is added so that the particulate water absorbing agent including the liquid permeability improving agent has improved saline flow conductivity (SFC) in comparison with SFC of a particulate water absorbing agent without the liquid permeability improving agent.

Specifically, to improve the liquid permeability, the liquid permeability improving agent used in the present invention is added as a spacer (Steric) or an ionic cross-linking agent, concurrently or separately with the addition of the surface cross-linking agent, to the water absorbent resin having a surface cross-linked normally by covalent bonding and surface polymerization with the use of the organic surface cross-linking agent. In other words, the particulate water absorbing agent preferably includes (1) an organic surface cross-linking agent used for covalent bonding, (2) a liquid permeability improving agent as a spacer (Steric) or an ionic cross-linking agent, and (3) a later-described lubrication improving agent, and is transported by (4) later-described pneumatic transportation. In the particulate water absorbing agent, the liquid permeability improving agent may be present in powder form, and/or as a coating whose molecules coat the water absorbent resin entirely (normally a solution of the liquid permeability improving agent is applied to the particulate water absorbing agent so as to coat the particulate water absorbing agent).

The liquid permeability improving agent is added concurrently with or after the addition of the surface cross-linking treatment. The liquid permeability improving agent serves as a spacer or widens a gap between particles of a swollen water absorbent resin by, e.g., ionic surface cross-linking effect, for improvement in the liquid permeability. The liquid permeability improving agent disadvantageously decreases a capillary absorption capacity of the particulate water absorbing agent. However, the particulate water absorbing agent has an excellent liquid permeability and capillary absorption capacity when controlled so as to have a particle size distribution within a specific range. Thus, although the water absorbent resin particles contain the liquid permeability improving agent, the particulate water absorbing agent has a high capillary absorption capacity. Further, the liquid permeability improving agent, when added to the particulate water absorbing agent controlled so as to have a specific particle size distribution, improves the liquid permeability significantly in comparison with conventional water absorbing agents. Specifically, the SFC normally varies greatly according to the particle size distribution and is lower with a smaller average grain diameter of the particulate water absorbing agent. However, the inventors of the present invention have found that the particulate water absorbing agent including the liquid permeability improving agent has SFC that is determined regardless of its particle size distribution and that depends only on a centrifuge retention capacity (CRC) of the particulate water absorbing agent, on the condition that the particle size distribution falls within a specific range. Also, the particulate water absorbing agent including the liquid permeability improving agent has capillary saline absorption capacity (CSF) with respect to 0.90 mass % physiological saline, the CSF depending on the particle size distribution. Therefore, adding the liquid permeability improving agent to the particulate water absorbing agent having a particle size distribution controlled so as to be a specific one produces a particulate water absorbing agent excelling in its SFC and CSF.

The liquid permeability improving agent used in the present invention is varied and therefore is not particularly limited. The liquid permeability improving agent is, e.g., an inorganic compound or an organic compound, preferably a hydrophilic inorganic compound. A water-insoluble fine powder, for example, is used as a spacer, while a polymeric polyhydric amine or polyhydric metal salt, for example, is used as an ionic cross-linking agent. Alternatively, the liquid permeability improving agent may be a compound combining the spacer and the ionic cross-linking agent (e.g., a water-insoluble cationic powder). The hydrophilicity regarded as preferable in the present invention is, for example, 70% or more as described in European Patent No. 0,629,411.

Examples of the liquid permeability improving agent usable in the present invention encompass (1) organic or inorganic water-insoluble fine particles and (2) water-soluble polyhydric metal particles as particles (spacer), and further encompass (3) water-soluble polyhydric metal (salt) and (4) a polymeric polyamine compound as non-particles (ionic cross-linking agent).

A first specific example of the liquid permeability improving agent usable in the present invention is an organic or inorganic water-insoluble fine powder having a weight median particle size of preferably 100 μm or less, more preferably 50 μm or less, even more preferably 10 μm or less, or most preferably 1 μm or less (where the lower limit is normally approximately 1 nm). More specifically, examples of inorganic water-insoluble fine powder usable as a spacer encompass: minerals such as silica, talc, kaolin, fuller's earth, bentonite, activated clay, barite, natural asphaltum, strontium ore, ilmenite, and perlite; hydrophilic amorphous silicas (e.g., drying process: ReolosilQS-20 available from Tokuyama; precipitating process: Sipernat 22S, Sipernat 2200 available from Evonik Degussa); and oxide complexes such as a complex including silicon oxide, aluminum oxide, and magnesium oxide (e.g., Attagel 50 available from Engelhard), a complex including silicon oxide and aluminum oxide, a complex including silicon oxide and magnesium oxide.

A second specific example of the liquid permeability improving agent usable in the present invention is water-soluble powder of a polyhydric metal, the water-soluble powder having a weight median particle size of preferably 100 μm or less, more preferably 50 μm or less, even more preferably 10 μm or less, or most preferably 1 μm or less. Specific examples of the polyhydric metal forming the water-soluble powder that may serve as a spacer or an ionic cross-linking agent encompass: aluminum compounds such as aluminum sulfate hydrate (tetradecahydrate to octadecahydrate) or anhydride, aluminum potassium sulfate didecahydrate, aluminum sodium sulfate didecahydrate, aluminum ammonium sulfate didecahydrate, aluminum chloride, aluminum polychloride, and aluminum oxide; and other polyhydric metal salts, polyhydric metal oxides, and polyhydric metal hydroxides.

A third specific example of the liquid permeability improving agent usable in the present invention is an aqueous solution or an aqueous dispersion solution of a polyhydric metal. The aqueous solution or aqueous dispersion solution may contain water-soluble powder of any polyhydric metal listed in the second specific example.

The following describes in further detail the polyhydric metal (salt) mentioned in the second and third specific examples.

Specific examples of the polyhydric metal salt usable in the present invention encompass sulfuric acid salt, nitric acid salt, carbonate, phosphoric acid salt, organic acid salt, and halide (e.g., chloride) of a metal selected from the group consisting of Zn, Be, Mg, Ca, Sr, Al, Fe, Mn, Ti, Zr, Ce, Ru, Y, and Cr, for example. Such specific examples further encompass the polyhydric metal salts disclosed in Japanese Unexamined Patent Publication (Tokukai) No. 2005-113117 (U.S. Patent Application Publication No. 2007/10613).

Among the above polyhydric metal salts, it is preferable to use a water-soluble polyhydric metal salt, and further, it is the most preferable to use a trivalent water-soluble polyhydric metal salt. Specific examples of the trivalent water-soluble polyhydric metal salt encompass aluminum chloride, aluminum polychloride, aluminum sulfate, aluminum nitrate, bis aluminum potassium sulfate, bis aluminum sodium sulfate, potassium alum, ammonium alum, sodium alum, sodium aluminate, iron (III) chloride, cerium (III) chloride, ruthenium (III) chloride, yttrium (III) chloride, and chromium (III) chloride.

In view of solubility with respect to absorbed liquid such as urine, it is preferable to use a salt having crystal water of the above trivalent water-soluble polyhydric metal salts. Such a salt is preferably an aluminum compound, for example. Among aluminum compounds, aluminum chloride, aluminum polychloride, aluminum sulfate, aluminum nitrate, bis aluminum potassium sulfate, bis aluminum sodium sulfate, potassium alum, ammonium alum, sodium alum, and sodium aluminate are more preferable. Among these, aluminum sulfate is the most preferable. An aluminum sulfate aqueous solution (preferably having an aluminum sulfate concentration of 90% or more with respect to saturation concentration) is usable most preferably.

A fourth specific example of the liquid permeability improving agent usable in the present invention is a polymeric polyamine compound, preferably a water-soluble polymeric polyamine, having an appropriately selected weight median molecular weight of 2000 or more, or preferably within a range from 4000 to 10000000. Specific examples of the water-soluble polymeric polyamine encompass polyethyleneimine and polyalylamine as well as a salt (e.g., hydrochloride) of them. They may be added independently or as a solution (particularly, an aqueous solution).

The first to fourth specific examples of the liquid permeability improving agent described above may be used independently, or two or more of them may be mixed for use as appropriate. The liquid permeability improving agent is contained in an amount determined depending on, e.g., compounds to be used and a combination of them. The amount preferably falls within a range from 0.001 to 5 parts by weight, more preferably within a range from 0.01 to 1 part by weight, even more preferably within a range from 0.02 to 0.7 part by weight, or particularly preferably within a range from 0.03 to 0.5 part by weight, in relation to 100 parts by weight (parts by mass) of the water absorbent resin. Containing the liquid permeability improving agent in an amount within the above range improves absorbency against pressure (AAP) under a pressure of 4.83 kPa and saline flow conductivity (SFC) of the particulate water absorbing agent. Containing the liquid permeability improving agent in an amount of more than 5 parts by weight may decrease the absorption capacity, whereas containing it in an amount of less than 0.001 part by weight may not achieve the effect of the liquid permeability improving agent. Further, changing the amount of the liquid permeability improving agent to be used allows adjustment of the liquid permeability and capillary absorption capacity of the particulate water absorbing agent.

The liquid permeability improving agent may be added by various methods. The liquid permeability improving agent is preferably mixed beforehand with water and/or a hydrophilic organic solvent as necessary to obtain an aqueous solution or an aqueous dispersion solution, and then is sprayed or dropped onto the water absorbent resin. Spraying the liquid permeability improving agent onto the water absorbent resin is more preferable. After the liquid permeability improving agent is added to the water absorbent resin, the resultant mixture may be dried. The above water is used in an amount determined as appropriate. The amount preferably falls within a range from 0.01 to 20 parts by weight, more preferably within a range from 0.1 to 10 parts by weight, or particularly preferably within a range from 0.5 to 5 parts by weight, in relation to 100 parts by weight of the water absorbent resin. The aqueous solution has a concentration of more than 50 weight %, or preferably more than 70 weight %, with respect to saturation concentration.

The water absorbent resin particles and the liquid permeability improving agent may be mixed using a mixer not having a particularly great mixing power. They may therefore be mixed using, e.g., a cracking machine or a sieving machine. Preferable examples of the mixer encompass a cylindrical mixer, a double-wall conical mixer, a V-shaped mixer, a ribbon-type mixer, a screw-type mixer, a flow-type oven rotary desk mixer, an air-flow-type mixer, a double-arm kneader, an internal mixer, a grinding kneader, a rotary mixer, a screw-type extruder, and a static mixer.

The liquid permeability improving agent is added to the water absorbent resin during or after a step of cooling the particulate water absorbing agent, preferably during the cooling step. The cooling step will be described later in detail.

(IV) Lubrication Improving Agent

The particulate water absorbing agent of the present invention includes the water absorbent resin that is subjected to the surface cross-linking treatment and that contains the liquid permeability improving agent, the water absorbent resin further containing a lubrication improving agent. Specific examples of the lubrication improving agent usable in the present invention encompass surface active agents and powdered lubricants. According to the above production method, the particulate water absorbing agent has a lubrication improving agent (e.g., a surface active agent or a powdered lubricant) on its surface.

<Lubricant>

A lubricant refers to a material that reduces friction (resistance) between two surfaces slidable along each other. When two objects are in contact with each other, respective surfaces of the objects may or may not, for example, be easily slidable along each other, i.e., a resistance may be large or small, depending on a condition of each surface. A lubricant makes objects more slidable along each other and reduces resistance between them.

The lubricant is varied and therefore not particularly limited.

The lubricant used in the present invention serves to reduce friction (resistance) between particles of the water absorbent resin. Use of the lubricant allows production of a particulate water absorbing agent having an increased loose bulk density and flow-down speed. The increased flow-down speed shortens a time for moving the particulate water absorbing agent from a container to a hopper and a time for filling a container with the particulate water absorbing agent from a hopper. This improves operating efficiency. These effects are similarly achieved by a later-described surface active agent and are major effects achieved by the particulate water absorbing agent of the present invention.

Further, the increased loose bulk density and flow-down speed may reduce powder stirring power necessary to produce the particulate water absorbing agent and energy necessary for pneumatic transportation. The reduction in the powder stirring power and energy necessary for the pneumatic transportation will not crush the water absorbent resin particles, therefore it is expected that deterioration in properties such as absorbency against pressure due to the pneumatic transportation can be avoided when the powder stirring power and energy necessary for the pneumatic transportation are low.

The lubricant usable in the present invention is present in a form not particularly limited. The lubricant is preferably in a solid state at room temperature (25° C.) at atmospheric pressure (0.101 MPa). The lubricant is more preferably in powder form. The lubricant of the present invention may be added as slurry or as an aqueous solution.

Examples of the lubricant encompass a hydrocarbon lubricant, a fatty acid lubricant, a fatty acid amide lubricant, an ester lubricant, an alcohol lubricant, and a metal soap lubricant. Among these, a metal soap lubricant is the most preferably because it serves not only as a lubricant, but also as a stabilization agent.

An example of the hydrocarbon lubricant is a low-polymer polyethylene. The low-polymer polyethylene is a polyethylene having a weight median molecular weight within a range from 1500 to 2000.

The fatty acid lubricant is not particularly limited, provided that the fatty acid lubricant acts as a lubricant. Among others, it is preferable to use a saturated or unsaturated fatty acid containing 12 or more carbon atoms ($C_{12}$ or more). More specifically, it is preferable to use a $C_{12}$ to $C_{28}$ saturated or unsaturated (preferably unsaturated) fatty acid. Examples of the fatty acid encompass lauric acid, myristic acid, palmitin acid, stearic acid, arachidic acid, and behenolic acid. Among these, it is preferable to use stearic acid because it is easy to obtain. The above fatty acid lubricants are preferably used in a form of fine particles. Further, the fatty acid lubricants are preferably free from any heavy metal that accelerates degradation of the water absorbent resin, the heavy metal including Fe and Ni. Also, the fatty acid lubricants are each preferably a purified product having a low iodine value and ester value.

The fatty acid amide lubricant is a compound derived from a fatty acid, the compound being represented by the general chemical formula $RCONH_2$. The fatty acid amide encompasses a primary amide ($R-CONH_2$), a secondary amide (($RCO)_2NH$), and a tertiary amide (($RCO)_3N$). Among these, it is preferable to use the primary amide. Examples of the primary amide encompass stearylamide, palmitylamide, oleylamide, methylenebisstearamide, and ethylenebissteara-mide. Among these, it is preferable to use methylenebisstearamide or ethylenebisstearamide because they excel in their compatibility, transparency, weather resistance, and non-adherence.

Examples of the ester lubricant encompass polyhydric alcohol esters of a fatty acid and fatty acid polyglycolic esters. A preferable polyhydric alcohol ester of a fatty acid is hydrogenated castor oil. A preferable fatty acid polyglycolic ester is ethylene glycol monostearate.

The alcohol lubricant is produced by substitution of a hydrogen atom of the hydrocarbon lubricant or the fatty acid lubricant by a hydroxyl group. The alcohol lubricant contains the same number of carbon atoms as mentioned above. The alcohol lubricant is not particularly limited; examples of the alcohol lubricant encompass a fatty alcohol having a single hydroxyl group in its molecule, such as cetyl alcohol and hydroxyl group; a glycol having two hydroxyl groups in its molecule, such as polyethylene glycol; and polyglycerol having three hydroxyl groups in its molecule. Polyethylene glycol and polyglycerol not only serve as a lubricant, but also serve to prevent charging.

The metal soap lubricant may be a compound disclosed, e.g., in U.S. Pat. No. 7,282,262. The metal soap lubricant includes a metal salt other than an alkali metal salt, such as fatty acid, petroleum acid, and polymer acid, which are all organic acids. The metal soap lubricant preferably includes: an organic acid having 7 carbon atoms; and polyhydric metal.

The powdered lubricant is normally present in a form of particles having a grain diameter not particularly limited. The grain diameter is normally smaller than the mass median particle size of the water absorbent resin. Ninety weight % or more of the particles have a grain diameter of 100 μm or less, preferably 50 μm or less, or more preferably 10 μm or less. The grain diameter has a lower limit of approximately 10 nm.

If the powdered lubricant is dispersed as slurry to be mixed with the water absorbent resin, the slurry has a lubricant concentration selected as appropriate depending, e.g., on the lubricant used, a kind of the dispersion solvent, and viscosity of the slurry. Therefore, the concentration is not particularly limited. The slurry has a solid content of the lubricant normally within a range from 0.0001 to 1 weight %, or preferably within a range from 0.001 to 0.5 weight %. When mixed with the lubricant, the water absorbent resin particles have a temperature normally equal to or higher than room temperature. To achieve a stable water absorbent property, flow-down speed, and bulk density of the particulate water absorbing agent, the water absorbent resin particles are mixed with the lubricant at a temperature of preferably 40° C. or more, or more preferably 50° C. or more. The water absorbent resin particles have a temperature when mixed with the lubricant, the temperature having an upper limit that is equal to or lower than a melting point of the lubricant. Temperatures higher than the melting point of the lubricant may decrease a mixing property of the water absorbent resin with respect to the lubricant.

The lubricant is added to the particulate water absorbing agent of the present invention in an amount adjusted as appropriate in accordance with a target bulk density and flow-down speed. The amount fails preferably within a range from 0.0001 to 1 weight %, or most preferably within a range from 0.001 to 0.5 weight %, in relation to 100 weight % of the water absorbent resin. When the lubricant is added in an amount within the above range, the amount is small. This prevents the water absorbent resin from having hydrophobicity and water repellency. This in turn increases the bulk density and flow-down speed without decreasing the water absorbent property. Further, the lubricant being added in an amount within the above range may, e.g., prevent decrease in the water absorbent property, the decrease being due to mechanical shock, and also may reduce the powder stirring power necessary to produce the particulate water absorbing agent and the energy necessary for the pneumatic transportation of the particulate water absorbing agent. On the other hand, the lubricant being added in an amount outside the above range is not only uneconomical, but also may decrease the water absorbent property.

<Surface Active Agent>

A surface active agent of the present invention has a hydrophilic portion and a lipophilic (hydrophobic) portion in its molecule. The surface active agent is strongly adsorbed on a surface of an object due to a balance between its hydrophilicity and lipophilicity, and consequently modifies a surface property of the object. Examples of the surface active agent usable in the present invention encompass anionic surface active agents, nonionic surface active agents, cationic surface active agents, and amphoteric surface active agents.

These surface active agents are each used in an amount of more than 0 and 0.2 part by weight or less, preferably within a range from 0.0001 to 0.2 part by weight, more preferably within a range from 0.0005 to 0.1 part by weight, even more preferably within a range from 0.001 to 0.05 part by weight, or most preferably within a range from 0.001 to 0.01 part by weight, in relation to 100 parts by weight of the water absorbent resin used. The surface active agent being added in an amount of less than 0.0005 part by weight may not sufficiently improve fluidity and bulk density of the particulate water absorbing agent. On the other hand, the surface active agent being added in an amount of more than 0.2 part by weight, 0.1 part by weight, or particularly 0.012 part by weight, not only problematically decreases surface tension of an absorbed liquid, but also uneconomically does not achieve an effect as much as reasonable from the amount of the surface active agent added.

The surface active agent used in the present invention has a HLB (hydrophilic-lipophilic balance) that is not particularly limited. The HLB falls preferably within a range from 8 to 18, more preferably within a range from 9 to 17, or even more preferably within a range from 10 to 17. The HLB being within the above range more suitably improves the fluidity and bulk density of the particulate water absorbing agent.

Examples of the anionic surface active agent encompass: fatty acid salt such as mixed fatty acid sodium soap, partially hydrogenated beef tallow fatty acid sodium soap, stearic acid sodium soap, oleic acid potassium soap, and castor oil potassium soap; alkyl sulfate ester salt such as sodium lauryl sulfate, sodium higher alcohol sulfate, and triethanolamine lauryl sulfate; alkylbenzene sulfonate such as sodium dodecyl benzene sulfonate; alkyl naphthalene sulfonate such as sodium alkyl naphthalene sulfonate; alkyl sulfosuccinate such as sodium dialkyl sulfosuccinate; alkyl diphenyl ether disulfonate such as sodium alkyl diphenyl ether disulfonate; alkyl phosphate such as potassium alkyl phosphate; polyoxyethylene alkyl (or alkyl aryl) sulfate ester such as sodium polyoxyethylene lauryl ether sulfate, polyoxyethylene alkyl ether sodium sulfate, polyoxyethylene alkyl ether triethanolamine sulphate, and polyoxyethylene alkyl phenyl ether sodium sulfate; special-reactivity anionic surface active agent; special carboxylic acid-type surface active agent; naphthalene sulfonate formalin condensate such as β-naphthalene sulfonate formalin condensate sodium salt and special-aromatic sulfonate formalin condensate sodium salt; special polycarboxylic acid polymeric surface active agent; and polyoxyethylene alkyl phosphate.

Examples of the nonionic surface active agent encompass: polyoxyethylene alkyl ether such as polyoxyethylene lauryl ether, polyoxyethylene cetyl ether, polyoxyethylene stearyl ether, polyoxyethylene oleyl ether, and polyoxyethylene higher alcohol ether; polyoxyethylene alkyl arylether such as polyoxyethylene nonylphenyl ether; polyoxyethylene derivative; sorbitan fatty acid ester such as sorbitan monolaurate, sorbitan monopalmitate, sorbitan monostearate, sorbitan monopalmitate, sorbitan monooleate, sorbitan trioleate, sorbitan sesquioleate, and sorbitan distearate; polyoxyethylene sorbitan fatty acid ester such as polyoxyethylene sorbitan monolaurate, polyoxyethylene sorbitan monolaurate, polyoxyethylene sorbitan monopalmitate, polyoxyethylene sorbitan monostearate, polyoxyethylene sorbitan monopalmitate, polyoxyethylene sorbitan monooleate, and polyoxyethylene sorbitan trioleate; polyoxyethylene sorbitol fatty acid ester such as tetraoleic acid polyoxyethylene sorbitol; glycerin fatty acid ester such as glycerol monostearate, glycerol monooleate, and self-emulsifying glycerol monostearate; polyoxyethylene fatty acid ester such as polyethylene glycol monolaurate, polyethylene glycol monostearate, polyethylene glycol distearate, and polyethylene glycol monooleate; polyoxyethylene alkylamine; polyoxyethylene hydrogenated castor oil; and alkyl alkanolamide.

Examples of the cationic surface active agent and amphoteric surface active agent encompass: alkyl amine salt such as coconut amine acetate and stearylamine acetate; quaternary ammonium salt such as lauryl trimethylammonium chloride, stearyl trimethylammonium chloride, cetyltrimethylammonium chloride, distearyl dimethylammonium chloride, and alkyl benzyl dimethylammonium chloride; alkylbetaine such as lauryibetaine, stearylbetaine, and lauryl carboxymethyl hydroxy ethyl imidazoliniumbetaine; and amine oxide such as lauryl dimethyl amine oxide. Use of the cationic surface active agent further makes a resultant hydrophilic polymer antibacterial.

The surface active agent may be a fluorine surface active agent. Use of the fluorine surface active agent makes the resultant hydrophilic polymer antibacterial. The fluorine surface active agent is varied; an example of it is one produced by substituting a hydrogen atom of a lipophilic group in a common surface active agent by a fluorine atom to obtain a perfluoroalkyl group. The surface active agent thus produced has a significantly higher surface activity.

The fluorine surface active agent may be anionic, nonionic, cationic, or amphoteric, when a hydrophilic group of the fluorine surface active agent is replaced. The fluorine surface active agent normally contains as a lipophilic group a fluorocarbon chain having the same structure. The carbon chain as a lipophilic group may be straight or branched. Typical examples of the fluorine surface active agent encompass the following:

Fluoroalkyl ($C_2$ to $C_{10}$) carboxylic acid, N-perfluorooctane sulfonyl disodium glutamate, 3-[fluoroalkyl ($C_6$ to $C_{11}$) oxy]-1-alkyl ($C_3$ to $C_4$) sodium sulfonate, 3-[ω-fluoroalkanoyl ($C_6$ to $C_8$)—N-ethylamino]-1-propane sodium sulfonate, N-[3-(perfluorooctane sulfonamide) propyl]-N,N-dimethyl-N-carboxymethylene ammoniumbetaine, fluoroalkyl ($C_{11}$ to $C_{20}$) carboxylic acid, perfluoroalkyl carboxylic acid ($C_7$ to $C_{13}$), perfluorooctane sulfonate diethanolamide, perfluoroalkyl ($C_4$ to $C_{12}$) sulfonate (Li, K, Na), N-propyl-N-(2-hydroxy ethyl) perfluorooctane sulfonamide, perfluoroalkyl ($C_6$ to $C_{10}$) sulfonamide propyl trimethylammonium salt, perfluoroalkyl ($C_6$ to $C_{10}$)—N-ethyl sulfonyl glycine salt (K), phosphate bis(N-perfluorooctyl sulfonyl-N-ethylamino ethyl), monoperfluoroalkyl ($C_6$ to $C_{16}$) ethyl phosphate, perfluoroalkyl quaternary ammonium iodide (product name: Fluorad FC-135, a cationic fluorine surface active agent available from Sumitomo 3M Limited), perfluoroalkyl alkoxylate (product name: Fluorad FC-171, a nonionic surface active agent available from Sumitomo 3M Limited), and perfluoroalkyl sulfonate potassium salt (product name: Fluorad FC-95 and Fluorad FC-98, anionic surface active agents available from Sumitomo 3M Limited)

The surface active agent of the present invention may be an organic metal surface active agent. The organic metal surface active agent used in the present invention contains molecules each having a main chain or a side chain of a metal such as Si, Ti, Sn, Zr, or Ge. The organic metal surface active agent preferably contains molecules each having a main chain of Si, or more preferably is a siloxane surface active agent. Typical examples of the organic metal surface active agent are described in, e.g., (New Edition: Surfactant Handbook written by Yoshida, Rondo, Ogaki, Yamanaka, published by Kogakutosho Limited (1966), page 34).

The surface active agent used in the present invention is not limited to those described above. In view of safety, a preferable surface active agent is, among the above surface active agents, a nonionic surface active agent, particularly a sorbitan fatty acid ester or a polyoxyethylene sorbitan fatty acid ester.

<Addition, Mixing, Etc. of the Lubrication Improving Agent>

The above lubrication improving agents may be used independently, or two or more of them may be used in combination. The lubrication improving agent may be added to the water absorbent resin by various methods. The lubrication improving agent is preferably mixed beforehand with water and/or a hydrophilic organic solvent as necessary to obtain an aqueous solution, and then is sprayed or dropped onto the water absorbent resin. Spraying the lubrication improving agent onto the water absorbent resin is more preferable. After the lubrication improving agent is added to the water absorbent resin, the resultant mixture may be dried.

The above water is used in an amount determined as appropriate. The amount preferably falls within a range from 0.01 to 20 parts by weight, more preferably within a range from 0.1 to 10 parts by weight, or particularly preferably within a range from 0.5 to 5 parts by weight, in relation to 100 parts by weight of the water absorbent resin. When the lubrication improving agent is a surface active agent, the aqueous solution has a concentration low enough not to have a clouding point at room temperature (25° C.).

The water absorbent resin particles and the lubrication improving agent may be mixed using a mixer not having a particularly great mixing power. They may therefore be mixed using, e.g., a cracking machine or a sieve. Preferable examples of the mixer encompass a cylindrical mixer, a double-wall conical mixer, a V-shaped mixer, a ribbon-type mixer, a screw-type mixer, a flow-type oven rotary desk mixer, an air-flow-type mixer, a double-arm kneader, an internal mixer, a grinding kneader, a rotary mixer, a screw-type extruder, and a static mixer.

(V) Particulate Water Absorbing Agent

<Appearance of the Particulate Water Absorbing Agent>

The particulate water absorbing agent of the present invention includes the water absorbent resin having a cross-linked structure in its surface, the surface having a site including the organic surface cross-linked layer, the liquid permeability improving agent layer, and the lubrication improving agent layer. The above site may be present either in an entire surface of the water absorbent resin or only in part of the surface of the water absorbent resin. When the above portion is present in part of the surface, the portion may be present in one or more parts in the surface.

The organic surface cross-linked layer is not necessarily present outside the water absorbent resin. According to the present invention, the organic surface cross-linked layer may be present inside the water absorbent resin, i.e., the organic surface cross-linked layer may be part of the water absorbent resin.

The particulate water absorbing agent of the present invention includes the water absorbent resin having a surface that has portion including the organic surface cross-linked layer, the liquid permeability improving agent layer, and the lubrication improving agent layer. The portion has respective layers, placed on one another, of the organic surface cross-linking agent, the liquid permeability improving agent, and the lubrication improving agent, in this order in a direction away from the water absorbent resin, i.e., in the order that they are added. If the organic surface cross-linking agent is added concurrently with the liquid permeability improving agent, the site includes a mixture of the organic surface cross-linked layer and the liquid permeability improving agent layer.

Each of the organic surface cross-linked layer, the liquid permeability improving agent layer, and the lubrication improving agent layer has a thickness not particularly limited. The respective thicknesses of the organic surface cross-linked layer, the liquid permeability improving agent layer, and the lubrication improving agent layer may be the same or different from one another. Further, each of the organic surface cross-linked layer, the liquid permeability improving agent layer, and the lubrication improving agent layer does not necessarily have a first surface facing the water absorbent resin, the first surface paralleling a second surface opposite from the first surface. Also, each of the organic surface cross-linked layer, the liquid permeability improving agent layer, and the lubrication improving agent layer may have different thicknesses at different positions locally. The liquid permeability improving agent layer has a thickness preferably within a range from 0.1 to 100 μm, more preferably within a range from 0.5 to 80 μm, or even more preferably within a range from 1 to 50 μm. The lubrication improving agent layer has a thickness preferably within a range from 0.01 to 100 μm, more preferably within a range from 0.05 to 50 μm, or even more preferably within a range from 0.1 to 10 μm.

<Shape of the Particulate Water Absorbing Agent>

A shape of the particulate water absorbing agent, i.e., a "particulate" shape, is, for example, a spherical shape, an ellipsoidal shape, a rod-like shape, or a granular shape formed by an agglomerate of spherical or ellipsoidal particles. Examples of the particulate shape further include: an irregularly pulverized shape obtained by pulverizing a polymer hydrogel prepared by polymerizing a monomer aqueous solution; and a granular shape obtained in the same manner. The particulate water absorbing agent preferably has a spherical shape or an ellipsoidal shape. The particulate water absorbing agent more preferably has: a granular shape formed by an agglomerate of spherical or ellipsoidal particles; or an irregularly pulverized shape obtained by pulverizing a polymer hydrogel prepared by polymerizing a monomer aqueous solution or a granular shape obtained in the same manner. Among these, the above irregularly pulverized shape or the granular shape is the most preferable.

When the particulate water absorbing agent has a spherical or ellipsoidal shape, it has a low mixing property with respect to a fiber material such as pulp during production of, e.g., an absorbing article. In addition, the particulate water absorbing agent tends to be easily removed from an absorbent core formed of a mixture of the particulate water absorbing agent and the fiber material. Thus, the use of the particulate water absorbing agent having a spherical or ellipsoidal shape problematically impedes uniform distribution of the particulate water absorbing agent in the absorbent core.

<Method for Producing the Particulate Water Absorbing Agent>

A method for producing a particulate water absorbing agent in accordance with the present invention includes the steps of: adding an organic surface cross-linking agent to a water absorbent resin having a cross-linked structure; adding a liquid permeability improving agent to the water absorbent resin concurrently with or after the addition of the organic surface cross-linking agent; and then adding a lubrication improving agent to the water absorbent resin. According to the method for producing a particulate water absorbing agent in accordance with the present invention, the liquid permeability improving agent is preferably added after the addition of the organic surface cross-linking agent. Further, the method for producing a particulate water absorbing agent in accordance with the present invention preferably includes: a thermal surface cross-linking step and a cooling step. In the thermal surface cross-linking step, the organic surface cross-linking agent is added, for a surface cross-linking treatment, to the water absorbent resin having a cross-linked structure. In the subsequent cooling step, the liquid permeability improving agent is added, followed by the addition of the lubrication improving agent. The organic surface cross-linking agent, the liquid permeability improving agent, and the lubrication improving agent are preferably added to the water absorbent resin in this order. The method for producing a particulate water absorbing agent in accordance with the present invention preferably includes a step of pneumatically transporting the particulate water absorbing agent. The pneumatic transportation of the present invention will be described later.

The method for producing a particulate water absorbing agent in accordance with the present invention is simply required to include the steps of: adding the organic surface cross-linking agent to the water absorbent resin having a cross-linked structure; adding the liquid permeability improving agent to the water absorbent resin concurrently with or after the addition of the organic surface cross-linking agent; and then adding the lubrication improving agent to the water absorbent resin. Other steps involved in the production are not particularly limited.

In the thermal surface cross-linking step, the water absorbent resin is heated at a temperature that falls within the range exemplified above. After the organic surface cross-linking agent is added, for a surface cross-linking treatment, to the water absorbent resin having a cross-linked structure, the water absorbent resin is preferably forcedly (externally) heated. In the cooling step, the material of the water absorbent resin is preferably cooled to a temperature that is below the heating temperature during the surface cross-linking treatment and that falls within a range from 100 to 20° C., more preferably within a range from 95 to 40° C., or even more preferably within a range from 80 to 45° C. The liquid permeability improving agent is preferably added during or after the step of cooling the particulate water absorbing agent, particularly preferably during the cooling step.

In the cooling step, the particulate water absorbing agent may be forcedly cooled with, e.g., a cooling device, or be left for spontaneous cooling. An example of the cooling device is prepared by replacing, by a cooling medium, the heating medium in the dryer used in the thermal surface cross-linking step.

The heating in the thermal surface cross-linking step and the cooling in the cooling step may be performed using the same device or different devices.

<Pneumatic Transportation>

The inventors of the present invention have found problems concerning actual production, the problems being peculiar to:

particulate water absorbing agents containing a liquid permeability improving agent such as polyhydric metal salt and water-insoluble inorganic fine powder; and a method for producing such particulate water absorbing agents. Specifically, the problems are: decreased transportability due to use of the liquid permeability improving agent; and decreased properties due to transportation after mixing with the liquid permeability improving agent. The inventors have further found that, while a process of producing water absorbent resins involves use of many various conveyors (e.g., screw conveyor, bucket conveyor, spring conveyor) that intermediately connect different steps, decrease in transportability and properties, the decrease being caused by the use of the liquid permeability improving agent, is significant in and peculiar to pneumatic transportation among other means.

As mentioned above, the method for producing a particulate water absorbing agent in accordance with the present invention preferably includes the step of pneumatically transporting the particulate water absorbing agent. The particulate water absorbing agent may be pneumatically transported by a pneumatic transportation method described, e.g., in Japanese Unexamined Patent Publication (Tokukai) No. 2004-345804, WO2007/104657, WO2007/104673, or WO2007/104676. In the pneumatic transportation step, the particulate water absorbing agent is transported using a low-density pneumatic transportation device or a high-density pneumatic transportation device, or specifically, through a pneumatic tube. Secondary air is blown through the pneumatic tube as necessary.

According to the method for producing a particulate water absorbing agent in accordance with the present invention, the particulate water absorbing agent is transported in the pneumatic transportation step over a transportation distance of preferably not less than 10 m and not more than 1000 m, more preferably not less than 10 m and not more than 200 m, or particularly preferably not less than 10 m and not more than 150 m. The term "transportation distance" as used herein refers to a horizontal and/or vertical distance between: a position at which the pneumatic transportation of the particulate water absorbing agent within the pneumatic tube starts; and a position at which the pneumatic transportation of the particulate water absorbing agent within the pneumatic tube ends. Generally, extending the transportation distance further than a certain level tends to decrease properties of the particulate water absorbing agent and/or plug the tube. However, the method for producing or transporting a particulate water absorbing agent in accordance with the present invention effectively prevents decrease in the properties of the particulate water absorbing agent and a plug in the tube even when the transportation distance is long.

The method for producing a particulate water absorbing agent in accordance with the present invention is a method for continuously producing the particulate water absorbing agent preferably in an amount of not less than 1 metric ton (Mt)/hr, more preferably in an amount of not less than 2 metric tons/hr, or particularly preferably in an amount of not less than 4 metric tons/hr. The above amount produced has an upper limit not particularly limited; the upper limit may be approximately 100 metric tons/hr. The particulate water absorbing agent is continuously produced by repeating the polymerization, drying, classification, and surface cross-linking.

As described above, the present invention solves the problems concerning actual production, i.e., decreased transportability due to use of a liquid permeability improving agent; and decreased properties due to transportation after mixing with the liquid permeability improving agent.

A method for transporting a particulate water absorbing agent in accordance with the present invention is as follows: the organic surface cross-linking agent and the liquid permeability improving agent are added to the water absorbent resin; the lubrication improving agent is then added to the water absorbent resin; and the water absorbent resin is pneumatically transported. The method for transporting a particulate water absorbing agent in accordance with the present invention is preferably as follows: an organic surface cross-linking agent is added to a water absorbent resin having a cross-linked structure; a liquid permeability improving agent is added to the water absorbent resin concurrently with or after the addition of the organic surface cross-linking agent; a lubrication improving agent is then added to the water absorbent resin; and the water absorbent resin is pneumatically transported. According to the method for transporting a particulate water absorbing agent in accordance with the present invention, the liquid permeability improving agent preferably contains water-insoluble fine powder or water-soluble polyhydric metal salt, while the lubrication improving agent preferably contains a surface active agent.

According to the method for transporting a particulate water absorbing agent in accordance with the present invention, the particulate water absorbing agent is transported over a transportation distance of preferably not less than 10 m and not more than 1000 m. Further, the method for transporting a particulate water absorbing agent in accordance with the present invention is preferably a method for continuously transporting the particulate water absorbing agent in an amount of not less than 1 metric ton/hr.

The following describes in detail the pneumatic transportation according to the present invention. The pneumatic transportation according to the present invention is widely applicable to transportation of an intermediate or a finished product during the process of producing the particulate water absorbing agent.

The pneumatic transportation method for the present invention will be described with reference to FIG. 1. FIG. 1 is a cross-sectional view schematically illustrating an embodiment of a high-density pneumatic transportation device. A particulate water absorbing agent to be transported is stored in a hopper 102. The particulate water absorbing agent to be transported is supplied from the hopper 102 via a lift tank 103 into a pneumatic tube 104. The compressor 106 generates compressed air, which causes the particulate water absorbing agent to be supplied from the hopper 102 into the pneumatic tube 104 and be transported through the pneumatic tube 104. As described above, the particulate water absorbing agent is transported to a hopper 108 by high-density pneumatic transportation involving the use of the compressed air. The pneumatic tube 104 may be provided with an air nozzle that serves to blow the secondary air. In this case, the secondary air, compressed by a compressor, is supplied via a secondary air supply tube to the air nozzle provided as appropriate in the pneumatic tube 104. The secondary air supplied to the air nozzle is blown into the pneumatic tube 104.

High-density pneumatic transportation requires less power than low-density pneumatic transportation. When the particulate water absorbing agent being transported through the pneumatic tube has a high density, a clump of the particulate water absorbing agent plugs the pneumatic tube entirely along its cross section. Most of the particulate water absorbing agent thus does not collide with a wall surface of the pneumatic tube. This prevents abrasion of the pneumatic tube and fracture of the particulate water absorbing agent. The particulate water absorbing agent is transported while plugging the pneumatic tube. When the particulate water absorbing agent is transported while plugging the pneumatic tube, the clump of the particulate water absorbing agent and air are ideally discrete. However, it is rare that the particulate water absorbing agent and air are discrete; in practice, part of the particulate water absorbing agent forms a still deposition layer on a bottom of the pneumatic tube. Other part of the particulate water absorbing agent forms a plug and is transported along the surface of the still deposition layer in an undulating movement. The deposition layer of the particulate water absorbing agent grows to form a hill-shaped clump and then a plug, which breaks up at some point. The particulate water absorbing agent repeats this behavior when transported.

The present invention refers to a device for the above high-density pneumatic transportation of the particulate water absorbing agent as a high-density pneumatic transportation device. In other words, a high-density pneumatic transportation device transports the particulate water absorbing agent through its pneumatic tube while forming a plug of the particulate water absorbing agent. The high-density pneumatic transportation device used in the method for transporting a particulate water absorbing agent in accordance with the present invention has an arrangement not particularly limited; the high-density pneumatic transportation device at least includes a pneumatic tube through which the particulate water absorbing agent is transported. Specifically, the high-density pneumatic transportation device according to the present invention includes: a storage tank such as a hopper for storing a particulate water absorbing agent; and a pneumatic tube through which the particulate water absorbing agent supplied from the storage tank is transported by compression. The high-density pneumatic transportation device according to the present invention further includes as necessary a secondary air supply tube that is connected to the pneumatic tube and that serves to supply the secondary air to the particulate water absorbing agent transported through the pneumatic tube by compression. The high-density pneumatic transportation device according to the present invention preferably includes a compressor for supplying primary air into the pneumatic tube. Further, the high-density pneumatic transportation device according to the present invention preferably includes another compressor for supplying the secondary air into the secondary air supply tube. Alternatively, the high-density pneumatic transportation device may include a single compressor for supplying both the primary air and the secondary air. The storage tank is preferably provided with a gas-tightly sealable valve in its bottom portion. The high-density pneumatic transportation device may be designed with reference to well-known art disclosed, e.g., in Japanese Unexamined Patent Publications (Tokukaihei) Nos. 6-191640 and 6-345264; and "Handbook of Chemical Engineers" (Society of Chemical Engineers, Japan published by Maruzen; page 890"16. 6. 2 Transportation Method Using Fluid").

The high-density pneumatic transportation device supplies the secondary air by a system not particularly limited. The secondary air is supplied by, e.g., a system for continuously supplying the secondary air, a system for blowing the secondary air from a bypass pipe, or a system for controlling blow of the secondary air. The secondary air is preferably supplied by a system for blowing the secondary air from a bypass pipe.

The secondary air refers to a gas supplied into the pneumatic tube at a position in midstream of the pneumatic tube. The secondary air may be compressed air in consideration of costs. In some particular cases in which, for example, the particulate water absorbing agent is reactive to oxygen, an inert gas such as nitrogen gas may be used as the secondary air. In this case, the primary air used to supply the particulate water absorbing agent into the pneumatic tube is also preferably an inert gas such as nitrogen gas.

The supply of the secondary air into the pneumatic tube facilitates prevention of the pneumatic tube being plugged by the particulate water absorbing agent. Transporting the particulate water absorbing agent with use of the secondary air further prevents decrease in the properties of the particulate water absorbing agent. Specifically, such transportation produces a significant effect in maintaining the properties such as a saline flow conductivity (SFC). A particulate water absorbing agent is a product that is assessed largely in terms of its properties. The method for producing and/or the method for transporting a particulate water absorbing agent in accordance with the present invention improves assessment of the particulate water absorbing agent and consequently makes the particulate water absorbing agent more competitive.

The secondary air is supplied at any number of positions. Further, the nozzle has any size. The plugging of the pneumatic tube by the particulate water absorbing agent is a phenomenon that occurs depending on multiple conditions such as nature and supply amount of the particulate water absorbing agent and size of the pneumatic tube. Therefore, the number of positions at which the secondary air is supplied and the size of the nozzle are determined in consideration of tendency of the particulate water absorbing agent to plug the pneumatic tube. The secondary air is supplied in an amount that is also not particularly limited. The amount is similarly determined in consideration of the tendency of the particulate water absorbing agent to plug the pneumatic tube.

According to the present invention, the particulate water absorbing agent is supplied into the pneumatic tube at a temperature of not less than 30° C., preferably not less than 40° C., or more preferably not less than 50° C. When the particulate water absorbing agent is supplied into the pneumatic tube at a temperature so maintained as to be a predetermined temperature or higher, decrease in the properties of the particulate water absorbing agent is prevented. Specifically, the maintaining of the temperature produces a significant effect in maintaining the properties such as the saline flow conductivity (SFC).

The particulate water absorbing agent to be supplied into the pneumatic tube has a temperature that is determined by measuring a temperature of the particulate water absorbing agent at an inlet of the pneumatic tube. The term "inlet of the pneumatic tube" refers to: a position at which the particulate water absorbing agent is supplied into the pneumatic tube for pneumatic transportation; and a region surrounding the position. The temperature of the particulate water absorbing agent has an upper limit that is not particularly limited. The particulate water absorbing agent having an excessively high temperature may decrease its properties. In addition, maintaining such a high temperature in the particulate water absorbing agent requires a large amount of energy. In view of these, the particulate water absorbing agent to be supplied into the pneumatic tube has a temperature of preferably not more than 100° C., more preferably not more than 95° C., or particularly preferably not more than 90° C.

The particulate water absorbing agent at an outlet of the pneumatic tube has a temperature of not less than 30° C., preferably not less than 40° C., or more preferably not less than 50° C. The term "outlet of the pneumatic tube" refers to: a position at which the particulate water absorbing agent is discharged from the pneumatic tube; and a region surrounding the position. When the particulate water absorbing agent being transported through the pneumatic tube has a temperature so maintained as to be a predetermined temperature or higher, decrease in the properties of the particulate water absorbing agent is prevented.

The temperature of the particulate water absorbing agent is so controlled as to be not less than 30° C. by a method that is not particularly limited. A preferable method is to provide heating means for externally heating the pneumatic tube, and the storage tank such as a hopper. For example, providing a copper pipe on an external wall of the storage tank such as a hopper and of the pneumatic tube and passing steam through the copper pipe allows maintaining, at a predetermined temperature or higher, the temperature of the particulate water absorbing agent before it is supplied into the pneumatic tube and while it is transported through the pneumatic tube.

The high-density pneumatic transportation device itself may be a conventionally well-known one. The high-density pneumatic transportation device may be provided, as necessary, with the heating means for maintaining, at the predetermined temperature or higher, the temperature of the particulate water absorbing agent being transported.

The high-density pneumatic transportation device has a size that is not particularly limited; the size depends, e.g., on the amount of the particulate water absorbing agent to be transported and/or the transportation distance. The transportation distance of the particulate water absorbing agent is controlled by adjusting a length of the pneumatic tube.

The method for producing a particulate water absorbing agent in accordance with the present invention includes the steps of adding an organic surface cross-linking agent and a liquid permeability improving agent to a water absorbent resin having a cross-linked structure, followed by adding a lubrication improving agent to the water absorbent resin. Thus, a particulate water absorbing agent produced by the method for producing a particulate water absorbing agent in accordance with the present invention includes a lubrication improving agent layer as its outermost layer, i.e., farthest away from the water absorbent resin. This improves fluidity exhibited both when the particulate water absorbing agent has absorbed moisture and when it is dry. This in turn facilitates handling the particulate water absorbing agent during its transportation and also reduces adherence of the particulate water absorbing agent to, e.g., devices in use. In addition, the particulate water absorbing agent, which includes a liquid permeability improving agent layer, has a superior liquid permeability. As a result, the saline flow conductivity (SFC) of the particulate water absorbing agent is reduced due to the pneumatic transportation by only a small degree. The particulate water absorbing agent is also superior in damage resistance. Furthermore, according to the method for producing a particulate water absorbing agent in accordance with the present invention, the secondary air is blown into the pneumatic tube during the pneumatic transportation step. This makes the above advantages of the present invention further significant.

<Other Components of the Particulate Water Absorbing Agent>

The particulate water absorbing agent of the present invention may be produced by performing, as necessary, a step of providing the particulate water absorbing agent with various functions, the step being exemplified by addition of a deodorant agent, an antibacterial agent, perfume, a foaming agent, a pigment, a dye, hydrophilic short fiber, a plasticizing agent, an adhesive, a fertilizer, an oxidizing agent, a reducing agent, water, salts, a chelating agent, a disinfectant, an anti-coloring agent, polyethylene glycol, hydrophilic polymer, a hydrophobic polymer such as paraffin, a thermoplastic resin such as polyethylene and polypropylene, a thermosetting resin such as polyester resin and urea resin. These additives are contained in an amount within a range generally from 0 to 30 parts by weight, preferably from 0 to 10 parts by weight, or more preferably from 0 to 1 part by weight, in relation to 100 parts by weight of the water absorbent resin.

The particulate water absorbing agent and the above additives are mixed with each other by a method that is not particularly limited; they may be mixed, e.g., by dry blending, in which they are mixed in powder form, or by wet blending, in which the additives are dispersed or dissolved in a solvent and then added to the particulate water absorbing agent.

The following describes the properties of the particulate water absorbing agent of the present embodiment.

As described above, the inventors of the present invention have found problems concerning actual production, the problems being peculiar to: particulate water absorbing agents containing a liquid permeability improving agent such as polyhydric metal salt and water-insoluble inorganic fine powder; and a method for producing such particulate water absorbing agents. Specifically, the problems are: decreased transportability (decreased productivity) due to use of the liquid permeability improving agent; and decreased properties due to transportation after mixing with the liquid permeability improving agent. The decrease in the properties involves a significant scale factor (decrease in the properties as compared to the properties observed in a laboratory). The scale factor suitably applies to the water absorbent resin and the particulate water absorbing agent described below.

The properties of the particulate water absorbing agent refer to those of a finished product in the production process, whereas the properties of the water absorbent resin refer to those during intermediate steps in the production process (particularly, properties of the water absorbent resin after the surface cross-linking or addition of the liquid permeability improving agent; more particularly, those after the addition of the liquid permeability improving agent, before the transportation).

<Mass Median Particle Size (D50), Etc. of the Particulate Water Absorbing Agent>

The particulate water absorbing agent of the present invention is prepared by granulation with, e.g., inorganic powder or hydrophilic organic solvent as necessary. The particulate water absorbing agent includes particles each having a particle diameter of not less than 150 μm and less than 850 μm at preferably 90 weight % (where an upper limit is 100%) or more, more preferably 95 weight % or more, or even more preferably 98 weight % or more, in relation to a mass of the particulate water absorbing agent. The particulate water absorbing agent is preferably so adjusted as to have a mass median particle size within the above range for the granulation. In view of this, the water absorbent resin before subjected to the surface cross-linking treatment preferably has a mass median particle size (D50) so controlled as to fall within the range of not less than 150 μm and less than 850 μm.

The water absorbent resin or the particulate water absorbing agent has a logarithmic standard deviation which shows a distribution of the mass median particle size, preferably within a range from 0.25 to 0.45, more preferably within a range from 0.25 to 0.42, even more preferably within a range from 0.25 to 0.40, or particularly preferably within a range from 0.25 to 0.38.

The water absorbent resin or the particulate water absorbing agent including particles (fine powder) of less than 150 μm in particle diameter at more than 10 weight % is not preferable because it poses a lot of problems as follows: the absorbent core will have a poor diffusion property of a liquid (e.g., blood or urine) absorbed to the absorbent core; The particulate water absorbing agent will be solubilized more easily because the particulate water absorbing agent used as the absorbent core has a larger area in contact with air; the fluidity of the particulate water absorbing agent after absorbed moisture will be decreased; a working environment will be deteriorated due to dust caused during the product ion of the particulate water absorbing agent and a sanitary material such as a diaper; a resultant wide particle size distribution will increase segregation. The logarithmic standard deviation being less than 0.25 would possibly decrease bulk density of the particulate water absorbing agent. In particular, when, for example, the particulate water absorbing agent of the present invention, which has improved powder fluidity, has a wide mass median particle size distribution and/or includes a large amount of fine powder, the particulate water absorbing agent has a significant segregation when in, e.g., a hopper or a bag. Thus, the particulate water absorbing agent with such segregation would cause instable quality of diapers to which it is used. The water absorbent resin or the particulate water absorbing agent including particles each having a particle diameter of 850 μm or more at more than 10 weight % is not preferably because it slows a water absorption rate of the particulate water absorbing agent. It also deteriorates a texture of an absorbing article including the particulate water absorbing agent and causes discomfort, thereby causing a user to feel uncomfortable. Thus, adjusting the mass median particle size within the above preferable range according to the present invention allows for production of a particulate water absorbing agent that excels in fluidity and bulk density, has no decrease in its water absorbing performance, and is free from the problem of segregation and the like.

The mass median particle size of the particulate water absorbing agent may be further adjusted in accordance with, e.g., an object or necessity, by granulating the particulate water absorbing agent by mixing with, e.g., insoluble fine particles and/or hydrophilic solvent, preferably water. The water absorbent resin or the particulate water absorbing agent preferably has a mass median particle size within a range from approximately 250 to 600 μm, more preferably within a range from approximately 300 to 500 μm, or most preferably within a range from approximately 350 to 450 μm.

The mass median particle size may be adjusted by dispersion polymerization and dispersion drying of the particulate water absorbing agent in a form of particles, as in the reversed phase suspension polymerization. When the particulate water absorbing agent is subjected to, e.g., the aqueous solution polymerization, the particulate water absorbing agent generally is dried and then is pulverized and classified, while fine powder thus caused is, e.g., granulated for recycling as necessary. This consequently allows the particulate water absorbing agent to have a mass median particle size adjusted to a specific one.

To provide the particulate water absorbing agent of the present invention, the water absorbent resin used in the present invention has a loose bulk density PIS K-3362) adjusted preferably within a range from 0.45 to 0.85 g/ml, more preferably within a range from 0.50 to 0.80 g/ml, or even more preferably within a range from 0.55 to 0.80 g/ml.

<Absorbency Against Pressure (AAP)>

The particulate water absorbing agent of the present invention has an absorbency against pressure (AAP) at a pressure (load) of 4.83 kPa, the absorbency being 17 g/g or more, preferably 18 g/g or more, more preferably 19 g/g or more, or particularly preferably 20 g/g or more. The water absorbent resin has a significant scale factor (decrease in the properties as compared to properties observed in a laboratory) in actual production. The scale factor applies to the water absorbent resin.

The particulate water absorbing agent of the present invention has an absorbency against pressure (AAP1) at a pressure (load) of 2.03 kPa, the absorbency being 20 g/g or more, preferably 22 g/g or more, more preferably 24 g/g or more, even more preferably 26 g/g or more, or particularly preferably 28 g/g or more. The absorbency against pressure has an upper limit that is not particularly limited and that is preferably high. However, from an economic viewpoint such as manufacturing cost, the absorbency against pressure is generally 50 g/g or less, or preferably 45 g/g or less.

The absorbency against pressure is herein evaluated for pressures (loads) of 4.83 kPa and 2.03 kPa with regard to a case where the absorbent core or the absorbent article such as a disposable diaper is used under a load from an infant in a lying or sitting position.

<Centrifuge Retention Capacity (CRC)>

The particulate water absorbing agent of the present invention has a centrifuge retention capacity (CRC) for a 0.90-weight % sodium chloride aqueous solution absorbed for 30 minutes, the centrifuge retention capacity having: a lower limit of preferably 10 g/g, more preferably 15 g/g, or even more preferably 20 g/g; and an upper limit of preferably 50 g/g, more preferably 40 g/g, or even more preferably 35 g/g. The centrifuge retention capacity falling outside the above range may lead to lack of high properties of the particulate water absorbing agent when the particulate water absorbing agent is used in diapers. The water absorbent resin before the surface cross-linking treatment has a centrifuge retention capacity (CRC) controlled preferably within a range from 10 to 60 g/g, or more preferably within a range from 25 to 40 g/g.

The water absorbent resin used in the present invention has a centrifuge retention capacity (CRC) that is decreased due to the surface cross-linking. The decrease in the CRC needs to be limited preferably to 95 to 50%, or more preferably to 90 to 60%, in comparison with the CRC before the surface cross-linking. The decrease in the CRC is adjusted as appropriate by adjusting, e.g., a kind and/or amount of the cross-linking agent, and/or a reaction temperature and/or time.

<Saline Flow Conductivity (SFC)>

A saline flow conductivity refers to a value indicative of liquid permeability exhibited when the particulate water absorbing agent is swollen. A higher SFC value indicates a higher liquid permeability.

The particulate water absorbing agent of the present invention has a saline flow conductivity (SFC) of preferably $10(10^{-7} \cdot cm^3 \cdot s \cdot g^{-1})$ or more, more preferably $30(10^{-7} \cdot cm^3 \cdot s \cdot g^{-1})$ or more, even more preferably $50(10^{-7} \cdot cm^3 \cdot s \cdot g^{-1})$ or more, or particularly preferably $80(10^{-7} \cdot cm^3 \cdot s \cdot g^{-1})$ or more. The water absorbent resin has a significant scale factor (decrease in the properties as compared to properties observed in a laboratory) in actual production. The scale factor applies to the water absorbent resin.

(VI) Pneumatic Transportation Method

In addition to the method for producing a particulate water absorbing agent, the present invention provides a method for transporting a particulate water absorbing agent, the method including the steps of: adding an organic surface cross-linking agent to a water absorbent resin having a cross-linked structure; adding a liquid permeability improving agent to the water absorbent resin concurrently with or after the addition of the organic surface cross-linking agent; adding a lubrication improving agent to the water absorbent resin concurrently or separately with the addition of the liquid permeability improving agent; and pneumatically transporting a resultant particulate water absorbing agent. The present invention further provides a method for producing a particulate water absorbing agent, the method including the above transportation method. The lubrication improving agent may be added concurrently with the addition of the liquid permeability improving agent. However, the lubrication improving agent is preferably added after the addition of the liquid permeability improving agent so as to provide an outermost surface for the particulate water absorbing agent.

The transportation method allows for industrial-scale production of a particulate water absorbing agent that is high in its properties (e.g., the SFC, AAP, particle size, CRC) and that is subjected to no decrease in its transportability (productivity) as well as in its properties.

The transportation method has detailed conditions identical to those described above, the conditions concerning, e.g.: a preferable water absorbent resin and its properties; a preferable liquid permeability improving agent (preferably, a polymeric polyamine compound, water-insoluble fine powder, or water-soluble polyhydric metal salt); a preferable lubrication improving agent (preferably, a surface active agent); a preferable transportation distance (not less than 10 m and not more than 1000 m); and a preferable transportation amount (continuous transportation of 1 Mt/hr or more).

(VII) Absorbent Core and/or Absorbing Article

The particulate water absorbing agent of the present invention has applications for water absorption and is widely used as an absorbent core and an absorbing article. Particularly, the particulate water absorbing agent is used in a sanitary material for absorbing a body fluid such as urine and blood. Each of the absorbent core and the absorbing article of the present invention includes a particulate water absorbing agent of the present invention.

The absorbent core refers to an absorbing agent molded, to include a particulate water absorbing agent and hydrophilic fiber as main components. The absorbent core is produced by molding the particulate water absorbing agent of the present invention and the hydrophilic fiber into a film shape, a tube shape, or a sheet shape, for example. The absorbent core contains the particulate water absorbing agent in an amount (core concentration) preferably within a range from 20 to 100 weight %, more preferably within a range from 30 to 100 weight %, or still more preferably within a range from 40 to 100 weight %, in relation to a total amount of the particulate water absorbing agent and the hydrophilic fiber. The absorbent core having a higher core concentration of the particulate water absorbing agent lowers the absorbent property of the particulate water absorbing agent significantly at the time of producing, e.g., the absorbent core and a disposable diaper. Further, the absorbent core is preferably thin; specifically, it preferably has a thickness within a range from, 0.1 to 5 mm.

The absorbing article includes the absorbent core, a liquid permeable front sheet, and a liquid impermeable back sheet. The absorbing article is produced as follows: First, for example, a fiber material and the particulate water absorbing agent are blended or placed on each other to produce the absorbent core. Next, the absorbent core is sandwiched by the liquid permeable front sheet and the liquid impermeable back sheet, and is provided with, e.g., an elastic member, a diffusion layer, and/or an adhesive tape. The resultant product is used as an absorbing article, particularly an adult incontinence pad and a sanitary napkin. The absorbent core is compression-molded to a density within a range from 0.06 to 0.50 g/cc and to a basic weight within a range from 0.01 to 0.20 g/cm². Examples of the fiber material used encompass: hydrophilic fiber; wood pulp that is, e.g., crushed; a cotton linter; a cross-linked cellulose fiber; rayon; cotton; wool; acetate; and vinylon. These fiber materials are preferably aerated.

The absorbing article of the present invention exhibits an excellent absorbent property. Specific examples of the absorbing article encompass sanitary materials such as: an adult disposable diaper, which has been greatly improved recently; a child diaper; a sanitary napkin: and a so-called incontinence pad. However, the absorbing article is not limited to these. The excellent absorbent property of the particulate water absorbent resin present in the absorbing article of the present invention achieves a smaller re-wet, highly dry feeling, and less burden exerted on users of the absorbing article and care givers.

EXAMPLES

The following Examples and Comparative Examples will explain the present invention more specifically. However, the present invention is not limited to them. In the Examples and Comparative Examples, all electric devices were operated at 100V and 60 Hz. The electric devices were operated at 25° C.±2° C. with a relative humidity of 50% RH, unless otherwise stated.

Note that the term "water absorbent resin composition" as used hereafter is synonymous with "particulate water absorbing agent."

[Method for Producing the Water Absorbent Resin]

First, 11.7 g (0.10 mol %) of polyethylene glycol diacrylate was dissolved in 5,438 g of an aqueous solution of sodium acrylate (monomer concentration: 39 weight %) having a neutralization ratio of 71.3 mol % in a reaction vessel which was a lidded stainless steel double-arm kneader with two sigma-type blades and a jacket (internal volume: 10 L) to obtain a reaction solution. Next, the reaction solution was deaerated for 30 minutes under nitrogen gas atmosphere. Then, 29.34 g of a 10-weight % aqueous solution of sodium persulfate and 24.45 g of a 0.1-weight % aqueous solution of L-ascorbic acid were added to the reaction solution while the mixture was stirred. Approximately 1 minute after the addition, polymerization started. The polymerization proceeded at temperatures within a range from 20 to 95° C. while the gel generated was crushed. Thirty minutes after the polymerization started, a cross-linked polymer hydrogel was taken out. The obtained water-containing gel-like cross-linked polymer had been crushed to approximately 5 mm or less in diameter. The crushed water-containing gel-like cross-linked polymer was spread on a 50-mesh (mesh size: 300 μm) metal gauze and dried in a heated airflow at 180° C. for 50 minutes. As a result, a water absorbent resin (1) was obtained, the water absorbent resin having an irregular shape, being easily pulverized, and being in forms of particles, powder, and powdery dried agglomerates.

The water absorbent resin (1) thus obtained was pulverized with a roll mill pulverizer (product name: "WML-type", available from Inoguchi Giken, Ltd.) and then was classified by a JIS standard sieve having a mesh size of 600 μm. Particles that had passed through the JIS standard sieve having a mesh size of 600 μm in the above operation were then classified by a JIS standard sieve having a mesh size of 150 μm. Water absorbent resin particles (1aF) that had passed through the JIS standard sieve having the mesh size of 150 μm were removed. This provided a particulate water absorbent resin (1a).

The removed water absorbent resin (1aF) was granulated in accordance with a method described in Granulation Example 1 of U.S. Pat. No. 6,228,930. The granulated particles were pulverized and classified through the same process. This provided a granulated water absorbent resin (1aA).

Then, 80 parts by weight of the water absorbent resin (1a) obtained as above and 20 parts by weight of the water absorbent resin (1aA) obtained as above were uniformly mixed, to obtain a water absorbent resin (A).

With 100 g of the water absorbent resin (A), a surface treatment agent including a mixture solution of 0.5 g of 1,4-butandiol, 1.0 g of propylene glycol, and 3.0 g of pure water was mixed. Next, a resultant mixture was heated at 210° C. for 30 minutes. Particles thus formed were disintegrated to a size small enough to pass through a JIS standard sieve having a mesh size of 600 μm. This provided a water absorbent resin (A1) having a cross-linked surface.

Table 1 shows a result of measurements of properties exhibited by the water absorbent resin (A1).

Example 1

As a liquid permeability improving agent, 1.0 part by weight of aluminum sulfate hydrate (tetradecahydrate to octadecahydrate) (available from KANTO CHEMICAL CO., INC.; mass median particle size: 182 μm, bulk density-density: 0.60 g/cm$^3$) was uniformly mixed with 100 parts by weight of the water absorbent resin (A1) thus obtained. Next, as a lubrication improving agent, 0.02 part by weight of 10-weight % polyoxyethylene (20) sorbitan mono stearate (product name: "Rheodol TW-S120V", available from Kao Corporation) was uniformly mixed. This provided a water absorbent resin composition (1) as a particulate water absorbing agent.

Comparative Example 1

With 100 parts by weight of the water absorbent resin (A1) obtained as above, 1.0 part by weight of aluminum sulfate hydrate (tetradecahydrate to octadecahydrate) (mass median particle size: 182 μm; bulk density: 0.60 g/cm$^3$) was uniformly mixed, to obtain a comparative water absorbent resin composition (2).

Comparative Example 2

With 100 parts by weight of the water absorbent resin (A1) obtained as above, 0.02 part by weight of 10-weight % polyoxyethylene (20) sorbitan monostearate aqueous solution was uniformly mixed. Next, 1.0 part by weight of aluminum sulfate hydrate (tetradecahydrate to octadecahydrate) (mass median particle size: 182 μm; bulk density: 0.60 g/cm$^3$) was uniformly mixed, to obtain a comparative water absorbent resin composition (3).

<Pneumatic Transportation Conditions>

Pneumatic transportation (air-pressure transportation) was performed with a force-feed pneumatic transportation device. The force-feed pneumatic transportation device primarily includes an air source, a particle supply section, a pneumatic tube, and a particle recovery section. The air source generates airflow, which transports particles. More specifically, the force-feed pneumatic transportation device transports particles with use of airflow caused by a difference in pressure between the particle supply section and the particle recovery section. The pneumatic transportation may involve use of a working fluid other than air, for example, an inert gas. The pneumatic transportation was performed under conditions of a transportation distance of 120 m and a terminal linear velocity of 27 m/second.

[Result of Measurements of Properties]

Table 1 compares a reference material and the composition obtained in Comparative Example 1 in measurements of: mass median particle size (D50); centrifuge retention capacity (CRC); absorbency against pressure (AAP) at a pressure of 4.83 kPa; and saline flow conductivity (SFC).

TABLE 1

| | Additive | Mass median particle size (D50) (μm) | Centrifuge retention capacity CRC (g/g) | Absorbency against pressure AAP (g/g) | Saline flow conductivity SFC ($10^{-7} \cdot cm^3 \cdot s \cdot g^{-1}$) |
|---|---|---|---|---|---|
| Reference material | None | 302 | 26 | 25 | 72 |
| Comparative example 1 | Liquid permeability improving agent (aluminum sulfate) | 304 | 26 | 24 | 168 |

As shown in Table 1, comparison between the water absorbent resin (A1) and the composition of Comparative Example 1 shows that the addition of the aluminum sulfate as a liquid permeability improving agent in Comparative Example 1 increased the saline flow conductivity (SFC). In other words, the comparison shows that adding a liquid permeability improving agent to a water absorbent resin having a cross-linked surface increases liquid permeability.

Table 2 evaluates the respective compositions of Example 1 and Comparative Examples 1 and 2 in measurements of: centrifuge retention capacity (CRC); absorbency against pressure (AAP) at a pressure of 4.83 kPa; and saline flow conductivity (SFC), before and after the pneumatic transportation.

TABLE 2

| | | PBPT | | | PAPT | | | |
|---|---|---|---|---|---|---|---|---|
| | Additive | CRC | AAP | SFC | CRC | AAP | SFC | PT |
| Example 1 | (1) PPIA (AS) (2) LIA (P(20)SM) | G | G | G | G | G | G | G |
| Comparative Example 1 | PPIA (AS) | G | G | G | G | P | P | P |

TABLE 2-continued

| | Additive | PBPT | | | PAPT | | | |
| | | CRC | AAP | SFC | CRC | AAP | SFC | PT |
|---|---|---|---|---|---|---|---|---|
| Comparative Example 2 | (1) LIA (P(20)SM) (2) PPIA (AS) | G | G | G | G | P | P | P |

[Abbreviations]
PBPT: properties before pneumatic transportation
PAPT: properties after pneumatic transportation
PT: pneumatic transportability
PPIA: liquid permeability improving agent
LIA: lubrication improving agent
AS: aluminum sulfate
P(20)SM: polyoxyethylene (20) sorbitan monostearate The numbers (1) and (2) show that (1) was added first and (2) was added later.

The evaluation represented by G and P is based on Example 1 being evaluated as G (Good). Each of Comparative Examples 1 and 2 is evaluated as G (Good) when it has a property equivalent to that of Example 1, and is evaluated as P (Poor) when it has a property lower than that of Example 1.

As shown in Table 2, comparison between Example 1 with Comparative Examples 1 and 2 reveals that the compositions of Comparative Examples 1 and 2 each showed a decrease in their evaluations of the absorbency against pressure (AAP) at a pressure of 4.83 kPa and the saline flow conductivity (SFC) after the pneumatic transportation, as compared to the composition of Example 1. Stated differently, the comparison reveals that adding additives, i.e., adding a liquid permeability improving agent and a lubrication improving agent in this order, to a water absorbent resin having a cross-linked surface results in a superior absorbency against pressure (AAP) at a pressure of 4.83 kPa and a superior saline flow conductivity (SFC), after pneumatic transportation. This shows that the water absorbent resin composition of Example 1 is an excellent particulate water absorbing agent that has high transportability and that only has a small decrease in its AAP and SFC, the decrease being due to the pneumatic transportation.

Production Example 1

A particulate water absorbent resin was continuously produced with a device (having a production capacity of approximately 1500 kg/h) for continuously producing a water absorbent resin. The device sequentially performs the following connected steps: a polymerizing step (for stationary polymerization on a belt); a gel-crushing step; a drying step; a pulverizing step; a classifying step; a surface cross-linking step (i.e., step for spraying a surface cross-linking agent, a heating step); a cooling step; a granulating step; and a step for transportation between the above steps.

The production specifically proceeds as follows: An acrylic acid partial sodium salt aqueous solution (concentration: 38 mass %) having a neutralization ratio of 75 mol % was prepared. The aqueous solution contained, as an internal cross-linking agent, 0.06 mol % (relative to the whole monomer) of polyethyleneglycol diacrylate (average number n (average polymerization degree)=9). The aqueous solution, i.e., a monomer aqueous solution (1), was continuously fed with a metering pump. Nitrogen gas was continuously blown into the pneumatic tube in midstream to keep an oxygen concentration at not more than 0.5 ppm.

Next, with the monomer aqueous solution (1), 0.14 (g) of sodium persulfate and 0.005 (monomer mol) of L-ascorbic acid were continuously mixed by line mixing. A resultant mixture was supplied onto a plane steel band having a dam at each end, to a thickness of 30 mm. The mixture was continuously subjected to stationary aqueous solution polymerization for 30 minutes, to obtain a cross-linked polymer hydrogel (2). The cross-linked polymer hydrogel (2) was crushed with a meat chopper having pores 7 mm in diameter, to approximately 1 mm. The crushed hydrogel was so spread on a porous plate as to have a thickness of 50 mm, the porous plate moving in a continuous circulation band dryer. The crushed hydrogel was then dried at 185° C. for 30 minutes, to obtain a dry polymer.

The dry polymer was all continuously supplied to a 3-stage roll mill (roll gaps: 1.0 mm, 0.55 mm, 0.42 mm, from top to bottom) for pulverization. The dry polymer thus pulverized was classified with a sieving device including metal screens 850 μm and 150 μm in mesh size respectively, to obtain a particulate water absorbent resin (3) (CRC=35 g/g) with approximately 98 mass % having a grain diameter within a range from 850 to 150 μm.

Production Example 2

A particulate water absorbent resin was continuously produced with a device (having a production capacity of approximately 1500 kg/h) for continuously producing a water absorbent resin. The device sequentially performs the following connected steps: a polymerizing step (for stationary polymerization on a belt); a gel-crushing step; a drying step; a pulverizing step; a classifying step; a surface cross-linking step (i.e., step for spraying a surface cross-linking agent, a heating step); a cooling step; a granulating step; and a step for transportation between the above steps.

The production specifically proceeds as follows: An acrylic acid partial sodium salt aqueous solution (concentration: 38 mass %) having a neutralization ratio of 74 mol % was prepared. The aqueous solution contained, as an internal cross-linking agent, 0.1 mol % (relative to the whole monomer) of polyethyleneglycol diacrylate (average number n (average polymerization degree)=9). The aqueous solution, i.e., a monomer aqueous solution (4), was continuously fed with a metering pump. Nitrogen gas was continuously blown into the pneumatic tube in midstream to keep an oxygen concentration at not more than 0.5 ppm.

Next, with the monomer aqueous solution (4), 0.14 (g) of sodium persulfate and 0.005 (monomer mol) of L-ascorbic acid were continuously mixed by line mixing. A resultant mixture was supplied onto a plane steel band having a dam at each end, to a thickness of 30 mm. The mixture was continuously subjected to stationary aqueous solution polymerization for 30 minutes to obtain a cross-linked polymer hydrogel (5). The cross-linked polymer hydrogel (5) was crushed with a meat chopper having pores 7 mm in diameter, to approximately 1 mm. The crushed hydrogel was so spread on a porous plate as to have a thickness of 50 mm, the porous plate moving in a continuous circulation band dryer. The crushed hydrogel was then dried at 185° C. for 30 minutes, to obtain a dry polymer.

The dry polymer was all continuously supplied to a 3-stage roll mill (roll gaps: 1.0 mm, 0.4 mm, 0.3 mm, from top to bottom) for pulverization. The dry polymer thus pulverized was classified with a sieving device including metal screens 710 μm and 150 μm in mesh size respectively, to obtain a particulate water absorbent resin (6) (CRC=33 g/g) with approximately 98 mass % having a grain diameter within a range from 710 to 150 μm.

Example 2

The water absorbent resin (3) obtained in Production Example 1 was continuously supplied to a high-speed continuous mixer (Turbulizer, 1000 rpm) at 1500 kg/hr. A surface treatment agent solution including a mixture solution of 0.3 part by mass of 1,4-butandiol, 0.5 part by mass of propylene glycol, and 2.7 parts by mass of pure water was sprayed, for mixing, onto 100 parts by mass of the water absorbent resin.

Next, a mixture obtained was continuously heated with a paddle dryer at 198° C. for 40 minutes. Then, the mixture was forcedly cooled with the same paddle dryer to 60° C. (cooling step). Next, the mixture was classified with a sieving device, to obtain particles having passed through an 850 μm mesh. Particles remaining on the screen 850 μm in mesh size were pulverized again and then mixed with the particles previously having passed through the 850 μm mesh, to obtain a granulated product all having passed through the 850 μm mesh, i.e., a water absorbent resin (A). Table 3 shows a result of measurements of properties exhibited by the water absorbent resin (A) thus obtained.

Example 3

In the cooling step, 1.0 part by mass of aluminum sulfate hydrate (tetradecahydrate to octadecahydrate) powder (available from KANTO CHEMICAL CO., INC.; mass median particle size: 182 μm, bulk density: 0.60 g/cm$^3$) as a liquid permeability improving agent was added to 100 parts by mass of the water absorbent resin in a zone of the cooling device, the zone having a temperature of approximately 90° C., and was uniformly mixed. Then, 0.02 part by mass of 10-mass % polyoxyethylene (20) sorbitan monostearate aqueous solution (product name: "Rheodol TW-S120V", available from Kao Corporation) as a lubrication improving agent was added in a zone of the cooling device, the zone having a temperature of approximately 70° C., and was uniformly mixed. Except for the above, an operation was performed in the same manner as in Example 2, to obtain a granulated product all having passed through the 850 μm mesh, i.e., a water absorbent resin composition. Table 3 shows a result of measurements of properties exhibited by the water absorbent resin composition (B1) thus obtained.

Example 4

The water absorbent resin (6) obtained in Production Example 2 was continuously supplied to a high-speed continuous mixer (Turbulizer, 1000 rpm) at 1500 kg/hr. A surface treatment agent solution including a mixture solution of 0.4 part by mass of 1,4-butandiol, 0.6 part by mass of propylene glycol, and 3.0 parts by mass of pure water was sprayed, for mixing, onto 100 parts by mass of the water absorbent resin.

Next, a mixture obtained was continuously heated with a paddle dryer at 200° C. for 40 minutes. Then, the mixture was forcedly cooled with the same paddle dryer to 60° C. (cooling step). In the cooling step, 1.0 part by mass of aluminum sulfate hydrate (tetradecahydrate to octadecahydrate) powder (available from KANTO CHEMICAL CO., INC.; mass median particle size: 182 μm, bulk density: 0.60 g/cm$^3$) as a liquid permeability improving agent was added to 100 parts by mass of the water absorbent resin in a zone of the cooling device, the zone having a temperature of approximately 90° C., and was uniformly mixed. Then, 0.02 part by mass of 10-mass % polyoxyethylene (20) sorbitan monostearate aqueous solution (product name: "Rheodol TW-S120V", available from Kao Corporation) as a lubrication improving agent was added in a zone of the cooling device, the zone having a temperature of approximately 70° C., and was uniformly mixed. Next, the water absorbent resin discharged from the cooling device was classified with a sieving device, to obtain particles having passed through a 710 μm mesh. Particles remaining on the screen 710 μm in mesh size were pulverized again and then mixed with the particles previously having passed through the 710 μm mesh, to obtain a granulated product all having passed through the 710 μm mesh, i.e., a water absorbent resin composition. Table 3 shows a result of measurements of properties exhibited by the water absorbent resin composition (B2) thus obtained.

Example 5

In the cooling step, 1.0 part by mass of aluminum sulfate aqueous solution (JIS K1450; tap water aluminum sulfate A1203: 8.1%) in place of the aluminum sulfate hydrate (tetradecahydrate to octadecahydrate) powder as a liquid permeability improving agent was added to 100 parts by mass of the water absorbent resin in a zone of the cooling device, the zone having a temperature of approximately 70° C., and was uniformly mixed. Then, 0.02 part by mass of 10-mass % polyoxyethylene (20) sorbitan monostearate aqueous solution (product name: "Rheodol TW-S120V", available from Kao Corporation) as a lubrication improving agent was added in a zone of the cooling device, the zone having a temperature of approximately 65° C., and was uniformly mixed. Except for the above, an operation was performed in the same manner as in Example 3, to obtain a granulated product all having passed through the 850 μm mesh, i.e., a water absorbent resin composition. Table 3 shows a result of measurements of properties exhibited by the water absorbent resin composition (B3) thus obtained.

Example 6

In the cooling step, 1.0 part by mass of aluminum sulfate aqueous solution (JIS K1450; tap water aluminum sulfate A1203: 8.1%) in place of the aluminum sulfate hydrate (tetradecahydrate to octadecahydrate) powder as a liquid permeability improving agent was added to 100 parts by mass of the water absorbent resin in a zone of the cooling device, the zone having a temperature of approximately 70° C., and was uniformly mixed. Then, 0.02 part by mass of 10-mass % polyoxyethylene (20) sorbitan monostearate aqueous solution (product name: "Rheodol TW-S120V", available from Kao Corporation) as a lubrication improving agent was added in a zone of the cooling device, the zone having a temperature of approximately 65° C., and was uniformly mixed. Except for the above, an operation was performed in the same manner as in Example 4, to obtain a granulated product all having passed through the 710 μm mesh, i.e., a water absorbent resin composition. Table 3 shows a result of measurements of properties exhibited by the water absorbent resin composition (B4) thus obtained.

Comparative Example 3

Except for absence of the 10-mass % polyoxyethylene (20) sorbitan monostearate aqueous solution as a lubrication improving agent, an operation was performed in the same manner as in Example 3. Table 3 shows a result of measurements of properties exhibited by the water absorbent resin composition (C1) thus obtained.

Comparative Example 4

Except for absence of the 10-mass % polyoxyethylene (20) sorbitan monostearate aqueous solution as a lubrication improving agent, an operation was performed in the same manner as in Example 4. Table 3 shows a result of measurements of properties exhibited by the water absorbent resin composition (C2) thus obtained.

Comparative Example 5

Except for absence of the 10-mass % polyoxyethylene (20) sorbitan monostearate aqueous solution as a lubrication improving agent, an operation was performed in the same manner as in Example 5. Table 3 shows a result of measurements of properties exhibited by the water absorbent resin composition (C3) thus obtained.

Comparative Example 6

Except for absence of the 10-mass % polyoxyethylene (20) sorbitan monostearate aqueous solution as a lubrication improving agent, an operation was performed in the same manner as in Example 6. Table 3 shows a result of measurements of properties exhibited by the water absorbent resin composition (C4) thus obtained.

Example 7

The water absorbent resin (3) obtained in Production Example 1 was continuously supplied to a high-speed continuous mixer (Turbulizer, 1000 rpm) at 1500 kg/hr. A surface treatment agent solution including a mixture solution of 0.3 part by mass of 1,4-butandiol, 0.5 part by mass of propylene glycol, and 2.7 parts by mass of pure water was sprayed, for mixing, onto 100 parts by mass of the water absorbent resin.

Next, a mixture obtained was continuously heated with a paddle dryer at 198° C. for 40 minutes. Then, the mixture was forcedly cooled with the same paddle dryer to 70° C. (cooling step). Next, 0.3 part by mass of water-insoluble silica fine particles (product name: "Aerogil 200CF", available from Nippon Aerogil, Ltd.; primary particle size: approximately 12 nm, BET specific surface area: approximately 200 m$^2$/g, drying loss: 1% or less) was added to 100 parts by mass of the water absorbent resin discharged from the cooling device. Then, 0.02 part by mass of 10-mass % polyoxyethylene (20) sorbitan monostearate aqueous solution (product name: "Rheodol TW-S120V", available from Kao Corporation) as a lubrication improving agent was added and was uniformly mixed. Next, the mixture was classified with a sieving device, to obtain particles having passed through an 850 μm mesh. Particles remaining on the screen 850 μm in mesh size were pulverized again and then mixed with the particles previously having passed through the 850 μm mesh, to obtain a granulated product all having passed through the 850 μm mesh, i.e., a water absorbent resin composition. Table 3 shows a result of measurements of properties exhibited by the water absorbent resin composition (B5) thus obtained.

Example 8

The water absorbent resin (6) obtained in Production Example 2 was continuously supplied to a high-speed continuous mixer (Turbulizer, 1000 rpm) at 1500 kg/hr. A surface treatment agent solution including a mixture solution of 0.4 part by mass of 1,4-butandiol, 0.6 part by mass of propylene glycol, and 3.0 parts by mass of pure water was sprayed, for mixing, onto 100 parts by mass of the water absorbent resin.

Next, a mixture obtained was continuously heated with a paddle dryer at 200° C. for 40 minutes. Then, the mixture was forcedly cooled with the same paddle dryer to 60° C. (cooling step). Next, 0.5 part by mass of water-insoluble silica fine particles (product name: "Aerogil 200CF", available from Nippon Aerogil, Ltd.; primary particle size: approximately 12 nm, BET ratio surface area: approximately 200 m2/g, drying loss: 1% or less) was added to 100 parts by mass of the water absorbent resin discharged from the cooling device. Then, 0.02 part by mass of 10-mass % polyoxyethylene (20) sorbitan monostearate aqueous solution (product name: "Rheodol TW-S120V", available from Kao Corporation) as a lubrication improving agent was added and was uniformly mixed. Next, the mixture was classified with a sieving device, to obtain particles having passed through a 710 μm mesh. Particles remaining on the screen 710 μm in mesh size were pulverized again and then mixed with the particles previously having passed through the 710 μm mesh, to obtain a granulated product all having passed through the 710 μm mesh, i.e., a water absorbent resin composition. Table 3 shows a result of measurements of properties exhibited by the water absorbent resin composition (B6) thus obtained.

Comparative Example 7

Except for absence of the 10-mass % polyoxyethylene (20) sorbitan monostearate aqueous solution as a lubrication improving agent, an operation was performed in the same manner as in Example 7. Table 3 shows a result of measurements of properties exhibited by the water absorbent resin composition (C5) thus obtained.

Comparative Example 8

Except for absence of the 10-mass % polyoxyethylene (20) sorbitan monostearate aqueous solution as a lubrication improving agent, an operation was performed in the same manner as in Example 8. Table 3 shows a result of measurements of properties exhibited by the water absorbent resin composition (C6) thus obtained.

Example 9

The water absorbent resin (3) obtained in Production Example 1 was continuously supplied to a high-speed continuous mixer (Turbulizer, 1000 rpm) at 1500 kg/hr. A surface treatment agent solution including a mixture solution of 0.3 part by mass of 1,4-butandiol, 0.5 part by mass of propylene glycol, 2.0 parts by mass of aluminum sulfate aqueous solution (JIS K1450; tap water aluminum sulfate A1203: 8.1%), and 1.7 parts by mass of pure water was sprayed, for mixing, onto 100 parts by mass of the water absorbent resin.

Next, a mixture obtained was continuously heated with a paddle dryer at 198° C. for 40 minutes. Then, the mixture was forcedly cooled with the same paddle dryer to 60° C. (cooling step). In the cooling step, 0.02 part by mass of 10-mass % polyoxyethylene (20) sorbitan monostearate aqueous solution (product name: "Rheodol TW-S120V", available from Kao Corporation) as a lubrication improving agent was added in a zone of the cooling device, the zone having a temperature of approximately 70° C., and was uniformly mixed. Next, the water absorbent resin discharged from the cooling device was classified with a sieving device, to obtain particles having passed through an 850 μm mesh. Particles remaining on the screen 850 μm in mesh size were pulverized again and then mixed with the particles previously having passed through the 850 μm mesh, to obtain a granulated product all having passed through the 850 μm mesh, i.e., a water absorbent resin composition. Table 3 shows a result of measurements of properties exhibited by the water absorbent resin composition (B7) thus obtained.

Example 10

The water absorbent resin (6) obtained in Production Example 2 was continuously supplied to a high-speed continuous mixer (Turbulizer, 1000 rpm) at 1500 kg/hr. A surface treatment agent solution including a mixture solution of 0.4 part by mass of 1,4-butandiol, 0.6 part by mass of propylene glycol, 2.0 parts by mass of aluminum sulfate aqueous solution (JIS K1450; tap water aluminum sulfate A1203: 8.1%), and 2.0 parts by mass of pure water was sprayed, for mixing, onto 100 parts by mass of the water absorbent resin.

Next, a mixture obtained was continuously heated with a paddle dryer at 200° C. for 40 minutes. Then, the mixture was forcedly cooled with the same paddle dryer to 60° C. (cooling step). In the cooling step, 0.02 part by mass of 10-mass % polyoxyethylene (20) sorbitan monostearate aqueous solution (product name: "Rheodol TW-S120V", available from Kao Corporation) as a lubrication improving agent was added in a zone of the cooling device, the zone having a temperature of approximately 70° C., and was uniformly mixed. Next, the water absorbent resin discharged from the cooling device was classified with a sieving device, to obtain particles having passed through a 710 μm mesh. Particles remaining on the screen 710 μm in mesh size were pulverized again and then mixed with the particles previously having passed through the 710 μm mesh, to obtain a granulated product all having passed through the 710 μm mesh, i.e., a water absorbent resin composition. Table 3 shows a result of measurements of properties exhibited by the water absorbent resin composition (B8) thus obtained.

Comparative Example 9

Except for absence of the 10-mass % polyoxyethylene (20) sorbitan monostearate aqueous solution as a lubrication improving agent, an operation was performed in the same manner as in Example 9. Table 3 shows a result of measurements of properties exhibited by the water absorbent resin composition (C7) thus obtained.

Comparative Example 10

Except for absence of the 10-mass % polyoxyethylene (20) sorbitan monostearate aqueous solution as a lubrication improving agent, an operation was performed in the same manner as in Example 10. Table 3 shows a result of measurements of properties exhibited by the water absorbent resin composition (C8) thus obtained.

Example 8

The water absorbent resin (3) obtained in Production Example 1 was continuously supplied to a high-speed continuous mixer (Turbulizer, 1000 rpm) at 1500 kg/hr. A surface treatment agent solution including a mixture solution of 0.3 part by mass of 1,4-butandiol, 0.5 part by mass of propylene glycol, and 2.7 parts by mass of pure water was sprayed, for mixing, onto 100 parts by mass of the water absorbent resin.

Next, a mixture obtained was continuously heated with a paddle dryer at 198° C. for 40 minutes. Then, the mixture was forcedly cooled with the same paddle dryer to 60° C. (cooling step). In the cooling step, 1.0 part by mass of aluminum sulfate aqueous solution (JIS K1450; tap water aluminum sulfate A1203: 8.1%) as a liquid permeability improving agent was added to 100 parts by mass of the water absorbent resin in a zone of the cooling device, the zone having a temperature of approximately 70° C., and was uniformly mixed. Then, 0.01 part by mass of stearic acid zinc was added as a lubrication improving agent to 100 parts by mass of the water absorbent resin in a zone of the cooling device, the zone having a temperature of approximately 65° C., and was uniformly mixed. Next, the water absorbent resin discharged from the cooling device was classified with a sieving device, to obtain particles having passed through an 850 μm mesh. Particles remaining on the screen 850 μm in mesh size were pulverized again and then mixed with the particles previously having passed through the 850 μm mesh, to obtain a granulated product all having passed through the 850 μm mesh, i.e., a water absorbent resin composition. Table 3 shows a result of measurements of properties exhibited by the water absorbent resin composition (B9) thus obtained.

[Pneumatic Transportation Condition 1]

The respective water absorbent resin compositions obtained in Examples and Comparative Examples were pneumatically transported continuously for approximately 12 hours using a high-density pneumatic transportation device. Each water absorbent resin composition was transported in an amount of 1500 kg/hr over a total transportation distance of 130 m, including a 110-m horizontal transportation and a 20-m vertical transportation, with a terminal linear velocity of approximately 10 m/sec. Table 3 shows properties of each water absorbent resin composition before and after the pneumatic transportation. Table 3 also shows how the pneumatic tube was blocked (pneumatic transportation status) during the pneumatic transportation, in accordance with the following criteria:

<Criteria for Determining a Pneumatic Transportation Status after 12 Hours>

A: The pneumatic tube was never blocked during the 12-hour pneumatic transportation.
B: The pneumatic tube was blocked once during the 12-hour pneumatic transportation.
C: The pneumatic tube was blocked twice or more during the 12-hour pneumatic transportation.

[Pneumatic Transportation Condition 2]

The respective water absorbent resin compositions obtained in Examples and Comparative Examples were pneumatically transported continuously for approximately 12 hours using a high-density pneumatic transportation device. Each water absorbent resin composition was transported in an amount of 1500 kg/hr over a total transportation distance of 130 m, including a 110-m horizontal transportation and a 20-m vertical transportation, with a terminal linear velocity of approximately 20 m/sec. Table 3 shows properties of each water absorbent resin composition before and after the pneumatic transportation. Table 3 also shows how the pneumatic tube was blocked (pneumatic transportation status) during the pneumatic transportation, in accordance with the same criteria as in Pneumatic transportation condition 1.

[Method for Measuring Properties)]

<Mass Median Particle Size (D50)>

Each water absorbent resin or water absorbent resin composition was sieved with JIS standard sieves having mesh sizes such as 850 μm, 710 μm, 600 μm, 500 μm, 425 μm, 300 μm, 212 μm, 150 μm, 106 μm, and 75 μm. Then, a residual percentage for each particle size was plotted on a logarithmic probability paper. A particle diameter corresponding to R=50% was read as a mass average particle diameter (D50).

Ten grams of each water absorbent resin or water absorbent resin composition was charged on the above JIS standard sieves under conditions of room temperature (20° C. to 25° C.) and a relative humidity of 50% RH. Each water absorbent resin or water absorbent resin composition was classified for 5 to 10 minutes with a low-tap-type sieve shaking apparatus (product name: "ES-65 sieve shaking apparatus", available from Iida Seisakusho, Ltd.).

As described, e.g., in U.S. Pat. No. 5,051,259, the mass average particle diameter (D50) is a particle diameter of a standard sieve which has a certain mesh size and corresponds to 50 weight % of the entire particles.

<Centrifuge Retention Capacity (CRC)>

First, 0.2 gram of each water absorbent resin or water absorbent resin composition was placed evenly in a bag of nonwoven fabric (60×60 mm). The bag was immersed in a largely excessive amount (e.g., 100 g or more) of a 0.9-weight % sodium chloride aqueous solution (physiological saline) having a temperature adjusted to 25° C. After 30 minutes, the bag was taken out of the solution and centrifuged in a centrifugal separator at 250 G for 3 minutes to remove water from the bag. A mass $W_2$ (g) of the nonwoven fabric bag was then measured. The same operation was carried out using neither a water absorbent resin nor a water absorbent resin composition, and a mass $W_1$ (g) was measured. A centrifuge retention capacity (g/g) was calculated from $W_1$ and $W_2$, in accordance with the following Formula 1:

$$\text{Centrifuge retention capacity(g/g)} = (\text{mass } W_2(g) - \text{mass } W_1(g))/\text{mass(g) of the water absorbent resin or water absorbent resin composition} - 1 \quad (1)$$

<Absorbency Against Pressure (AAP) at a Pressure of 4.83 kPa>

A load was prepared that was so adjusted as to apply a pressure of 4.83 kPa (0.7 psi). Then, 0.90 g of each water absorbent resin or water absorbent resin composition was evenly spayed onto a 400-mesh metal gauze (mesh size: 38 μm) attached to the bottom of a plastic cylinder having a diameter of 60 mm. The above load was then placed on the metal gauze. This set of a measuring device was measured for mass $W_3$ (g).

Next, a glass filter (Sougo Rikagaku Glass Seisakusho Co., Ltd.; diameter of fine pores: 100 to 120 μm) having a diameter of 90 mm was placed in a petri dish having a diameter of 150 mm. Then, a 0.90-weight % sodium chloride aqueous solution (20 to 25° C.) was added until it was flush with the top surface of the glass filter.

A sheet of filter paper (product name: "JIS P3801, No. 2", Advantec Toyo Kaisha, Ltd.; thickness: 0.26 mm, diameter of retained particles: 5 μm) having a diameter of 90 mm was placed on a surface of the aqueous solution in such a manner that the entire surface of the sheet was wet. Also, an excess liquid was removed.

The set of a measuring device was placed on the wet filter paper so that the paper could absorb the solution under the load. An hour (60 minutes) later, the set of a measuring device was lifted, and its mass $W_4$ (g) was measured. The values were substituted into $W_3$ and $W_4$ in the following Formula 2 to calculate an absorption capacity against pressure (g/g).

$$\text{Absorption against pressure(g/g) under a pressure of } 4.83 \text{ kPa} = (W_4(g) - W_3(g))/\text{mass(g) of the water absorbent resin or water absorbent resin composition} \quad (2)$$

<Saline Flow Conductivity (SFC)>

A saline flow conductivity (SFC) refers to a value indicative of liquid permeability of a water absorbent resin or water absorbent resin composition in a swelling state. A high SFC value shows a high liquid permeability. A test was performed similarly to a saline flow conductivity (SFC) test described in U.S. Patent No. 2004-0106745.

The test was performed specifically as follows: First, 0.90 g of each water absorbent resin or water absorbent resin composition evenly contained in a cell was swelled in a synthesized urine under a pressure of 0.3 psi (2.07 kPa) for 60 minutes, and a height of a gel layer was recorded. Then, a 0.69-weight % sodium chloride aqueous solution was made to flow from a tank to pass through the swollen gel layer at a constant hydrostatic pressure under a pressure of 0.3 psi (2.07 kPa).

A glass tube was inserted in the tank. The glass tube was so placed as to have a lower end adjusted in such as position that the 0.69-weight % sodium chloride aqueous solution in the cell maintained its liquid level at 5 cm above a bottom of the swelling gel. The 0.69-weight % sodium chloride aqueous solution contained in the tank was supplied to the cell via an L-shaped tube with a cock. A collecting container for collecting liquid having passed through the gel layer was disposed under the cell. The collecting container was placed on an even balance. The cell had an inside diameter of 6 cm and was provided with a No. 400 stainless metal gauze (38 μm in mesh size) on a bottom of a lower portion of the cell. A hole which allowed liquid to pass through was provided on a lower portion of a piston. A glass filter having a high permeability was provided on the bottom of the piston so that no water absorbent resin or water absorbent resin composition, or no swelling gel of it, could enter into the hole. The cell was placed on a table for the cell. The table was positioned on the stainless metal gauze which did not prevent the liquid from passing through.

The above synthesized urine was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of ammonium dihydrogen phosphate, and 994.25 g of pure water.

The SFC test was carried out at room temperature (20 to 25° C.). By using a computer and a scale, an amount of liquid passing through the gel layer at intervals of 20 seconds was recorded for 10 minutes as a time function. A flow rate Fs(t) of the solution passing through the swollen gel (mainly between its particles) was determined in terms of g/s by dividing an increasing weight (g) by an increasing time (s). A time in which a constant hydrostatic pressure and a stable flow rate had been obtained was set as "ts". The flow rate calculated between "ts" and a ten-minute interval was used to calculate a value of Fs (t=0), i.e., a first flow rate of the solution passing through the gel layer. Fs (t=0) was calculated by extrapolating, into t=0, a result obtained by carrying out least square of Fs (t) and a duration. The saline flow conductivity (liquid permeation rate under pressure) was determined, using Formula 3 below. The unit of the liquid permeation rate under pressure was $(10^{-7} \times cm^3 \times s \times g^{-1})$.

$$\text{Liquid permeation rate under pressure} = (Fs(t=0) \times L0)/(\rho < A \times \Delta P) \quad (3)$$

Fs (t=0): a flow rate in unit of g/s
L0: a height of the gel layer in unit of cm
ρ: a density (1.003 g/cm$^3$) of NaCl solution
A: an area (28.27 cm$^2$) on the upper side of the gel layer in the cell
ΔP: a hydrostatic pressure (4920 dyne/cm$^2$) exerted to the gel layer Table 3 shows results of evaluation of: centrifuge retention capacity (CRC); absorbency against pressure (AAP) at a pressure of 4.83 kPa; saline flow conductivity (SFC); and how the pneumatic tube was blocked during pneumatic transportation, each measured for Examples 2 through 11 and Comparative Examples 3 through 10, before and after the pneumatic transportation.

TABLE 3

| | PPIA | LIA | Before PT | | | After PT (PT condition 1) | | | | After PT (PT condition 2) | | | |
|---|---|---|---|---|---|---|---|---|---|---|---|---|---|
| | | | CRC (g/g) | AAP (g/g) | SFC ($10^{-7}$) | CRC (g/g) | AAP (g/g) | SFC ($10^{-7}$) | PTS | CRC (g/g) | AAP (g/g) | SFC ($10^{-7}$) | PTS |
| Ex 2 | None | None | 30.5 | 25.1 | 32 | 30.5 | 25.1 | 32 | A | 30.7 | 24.8 | 26 | A |
| Ex 3 | ASP | P(20)SM | 30.0 | 24.5 | 65 | 30.0 | 24.4 | 63 | A | 30.3 | 24.2 | 60 | A |
| Ex 4 | ASP | P(20)SM | 27.0 | 23.7 | 130 | 27.0 | 23.6 | 128 | A | — | — | — | — |
| Ex 5 | ASAS | P(20)SM | 30.5 | 24.3 | 53 | 30.0 | 24.3 | 53 | A | 30.2 | 24.2 | 50 | A |
| Ex 6 | ASAS | P(20)SM | 27.0 | 23.5 | 120 | 27.2 | 23.4 | 118 | A | — | — | — | — |
| Ex 7 | WIS | P(20)SM | 30.0 | 23.0 | 60 | 30.0 | 23.0 | 60 | A | 30.3 | 22.8 | 57 | A |
| Ex 8 | WIS | P(20)SM | 27.0 | 22.5 | 130 | 27.0 | 22.5 | 129 | A | — | — | — | — |
| Ex 9 | ASAS/SCLA | P(20)SM | 30.0 | 24.2 | 40 | 30.1 | 24.1 | 40 | A | 30.4 | 24.0 | 37 | A |
| Ex 10 | ASAS/SCLA | P(20)SM | 27.0 | 23.5 | 100 | 27.0 | 23.4 | 99 | A | — | — | — | — |
| Ex 11 | ASAS | SAZ | 30.5 | 24.2 | 53 | 30.0 | 24.2 | 53 | A | 30.2 | 24.0 | 49 | A |
| CEx 3 | ASP | None | 30.0 | 24.5 | 65 | 30.0 | 24.4 | 63 | B | 30.5 | 24.0 | 55 | A |
| CEx 4 | ASP | None | 27.0 | 23.7 | 130 | 27.0 | 23.6 | 128 | B | 27.2 | 23.2 | 117 | A |
| CEx 5 | ASAS | None | 30.5 | 24.3 | 53 | 30.5 | 24.2 | 52 | C | 31.0 | 23.8 | 46 | B |
| CEx 6 | ASAS | None | 27.0 | 23.5 | 120 | 27.0 | 23.4 | 118 | C | 26.5 | 23.0 | 110 | B |
| CEx 7 | WIS | None | 30.0 | 23.0 | 60 | 30.0 | 22.9 | 59 | B | 30.0 | 22.5 | 53 | A |
| CEx 8 | WIS | None | 27.0 | 22.5 | 130 | 27.0 | 22.4 | 127 | B | 27.5 | 22.0 | 115 | A |
| CEx 9 | ASAS/SCLA | None | 30.0 | 24.2 | 40 | 30.0 | 24.1 | 38 | C | 30.7 | 23.5 | 34 | B |
| CEx 10 | ASAS/SCLA | None | 27.0 | 23.5 | 100 | 27.0 | 23.4 | 98 | C | 27.3 | 23.0 | 90 | B |

[Abbreviations]
Ex: Example,
CEx: Comparative Example,
PPIA: liquid permeability improving agent
LIA: lubrication improving agent,
PT: pneumatic transportation,
PTS: pneumatic transportation status,
ASP: aluminum sulfate powder
ASAS: aluminum sulfate aqueous solution,
WIS: water-insoluble silica,
SAZ: stearic acid zinc
SCLA: surface cross-linking agent,
P(20)SM: polyoxyethylene (20) sorbitan monostearate As shown in Table 3, comparison between Examples 2 through 11 and Comparative Examples 3 through 10 reveals that the pneumatic tube was blocked more often during the pneumatic transportation in Comparative Examples 3 through than in Examples 2 through 11 under pneumatic transportation condition 1, i.e., under the condition of the terminal linear velocity being approximately 10 m/sec (low velocity). This shows that the pneumatic transportation status was deteriorated in Comparative Examples 3 through 10. The comparison also reveals that the AAP and SFC in Comparative Examples 3 through 10 decreased due to the pneumatic transportation more than those in Examples 2 through 11 under pneumatic transportation condition 2, i.e., under the condition of the terminal linear velocity being approximately 20 m/sec (high velocity). In other words, the comparison shows that the water absorbent resin composition of each of Examples 2 through 11 was a particulate water absorbing agent that had an excellent pneumatic transportation status and that had superior properties such as fluidity and damage resistance after pneumatic transportation, as compared to the water absorbent resin composition of each of Comparative Examples 3 through 10.

As described above, the inventors of the present invention have found problems peculiar to: particulate water absorbing agents containing a liquid permeability improving agent such as polyhydric metal salt and water-insoluble inorganic fine powder; and a method for producing such particulate water absorbing agents. Specifically, the problems are: decreased transportability due to use of a liquid permeability improving agent; and decreased properties due to transportation (in particular, pneumatic transportation) after mixing with the liquid permeability improving agent.

In order to solve the above problems, a method for producing a particulate water absorbing agent in accordance with the present invention, as described above, includes the steps of: adding an organic surface cross-linking agent to a water absorbent resin having a cross-linked structure; adding a liquid permeability improving agent to the water absorbent resin concurrently with or after the step of adding the organic surface cross-linking agent; and adding a lubrication improving agent to the water absorbent resin after the step of adding the liquid permeability improving agent.

The present invention thus provides a particulate water absorbing agent and a method for producing the same, the particulate water absorbing agent having superior pneumatic transportability, maintaining an effect of a liquid permeability improving agent, and excelling in properties such as fluidity and damage resistance after pneumatic transportation.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, the particulate water absorbing agent maintains its water absorbent property and an effect of a liquid permeability improving agent, and also excels in properties such as fluidity and damage resistance after pneumatic transportation. The water absorbing article of the present invention includes the particulate water absorbing agent and thus exhibits superior properties such as absorbent property. The absorbing article is widely applicable, e.g., to sanitary materials such as an adult disposable diaper, which has been greatly improved recently, a child diaper, a sanitary napkin, and a so-called incontinence pad.

The invention claimed is:

1. A method for producing a particulate water absorbing agent including (i) a water absorbent resin having been subjected to a surface cross-linking treatment with use of an organic surface cross-linking agent and (ii) a liquid permeability improving agent, the method comprising the steps of:
   (a) providing a water absorbent resin by cross-linking and polymerizing an unsaturated monomer containing an acid group and/or its salt;
   (b) after the step (a), forming a surface cross-linked layer on the water absorbent resin by adding an organic surface cross-linking agent to the water absorbent resin having a cross-linked structure;
   (c) forming a liquid permeability improving agent layer on the water absorbent resin by adding a liquid permeability improving agent to the water absorbent resin concurrently with or after the step of adding the organic surface cross-linking agent;
   (d) forming a lubrication improving agent layer on the water absorbent resin by adding a lubrication improving agent to the water absorbent resin concurrently with or after the step of adding the liquid permeability improving agent; and
   (e) pneumatically transporting a particulate water absorbing agent with use of a low-density pneumatic transportation device or a high-density pneumatic transportation device, the particulate water absorbing agent being obtained by carrying out the steps (b), (c) and (d).

2. The method for producing a particulate water absorbing agent according to claim 1, wherein the liquid permeability improving agent is added after the organic surface cross-linking agent is added.

3. The method for producing a particulate water absorbing agent according to claim 1, wherein the liquid permeability improving agent includes a polymeric polyamine compound, water-insoluble fine powder, or water-soluble polyhydric metal salt.

4. The method for producing a particulate water absorbing agent according to claim 1, wherein the liquid permeability improving agent is added in a form of an aqueous solution or an aqueous dispersion solution.

5. The method for producing a particulate water absorbing agent according to claim 1, wherein the lubrication improving agent includes a surface active agent or a lubricant.

6. The method for producing a particulate water absorbing agent according to claim 1, further comprising: a thermal surface cross-linking step and a cooling step,
wherein:
   the thermal surface cross-linking step includes the step of adding organic surface cross-linking agent to the water absorbent resin and performing a surface cross-linking treatment; and
   concurrently with or after the cooling step subsequent to the thermal surface cross-linking step, the step of adding the liquid permeability improving agent and the step of adding the lubrication improving agent are performed in this successive order.

7. The method for producing a particulate water absorbing agent according to claim 1, wherein:
   the lubrication improving agent is a surface active agent selected from the group consisting of an anionic surface active agent, a nonionic surface active agent, a cationic surface active agent, and an amphoteric surface active agent; and
   the surface active agent is added in an amount of more than 0 part by weight and not more than 0.2 part by weight in relation to 100 parts by weight of the water absorbent resin.

8. The method for producing a particulate water absorbing agent according to claim 1, wherein:
   the lubrication improving agent is a lubricant selected from the group consisting of a hydrocarbon lubricant, a fatty acid lubricant, a fatty acid amide lubricant, an ester lubricant, an alcohol lubricant, and a metal soap lubricant; and
   the lubricant is added in an amount within a range from 0.0001 to 1 weight % in relation to the water absorbent resin.

9. The method for producing a particulate water absorbing agent according to claim 1, wherein the lubrication improving agent is an alcohol lubricant.

10. The method for producing a particulate water absorbing agent according to claim 1, wherein the lubrication improving agent is a powdered lubricant.

11. The method of producing a particulate water absorbing agent according to claim 1, wherein the particulate water absorbing agent is supplied into a pneumatic tube at a temperature of not less than 30° C.

12. The method for producing a particulate water absorbing agent according to claim 1, wherein the particulate water absorbing agent is supplied into a pneumatic tube at a temperature within a range from 40 to 100° C.

13. The method for producing a particulate water absorbing agent according to claim 1, wherein the particulate water absorbing agent has a saline flow conductivity (SFC) of 10 ($10^{-7} \cdot cm^3 \cdot s \cdot g^{-1}$) or more.

14. The method for producing a particulate water absorbing agent according to claim 1, wherein the particulate water absorbing agent is transported over a transportation distance of not less than 10 m and not more than 1000 m.

15. The method for producing a particulate water absorbing agent according to claim 1, wherein the particulate water-absorbing agent is continuously transported in an amount of not less than 1 metric ton/hr.

16. The method for producing a particulate water absorbing agent according to claim 1, wherein the lubricant improving agent is added after the step of adding the liquid permeability improving agent.

* * * * *